US012305202B2

(12) United States Patent
Zhu et al.

(10) Patent No.: US 12,305,202 B2
(45) Date of Patent: May 20, 2025

(54) POLYPEPTIDE COMPOSITION

(71) Applicants: JECHO INSTITUTE, CO., LTD., Shanghai (CN); JECHO LABORATORIES, INC., Frederick, MD (US)

(72) Inventors: Jianwei Zhu, Shanghai (CN); Jing Wang, Shanghai (CN); Lei Han, Shanghai (CN); Junsheng Chen, Shanghai (CN); Yueqing Xie, Shanghai (CN); Hua Jiang, Shanghai (CN)

(73) Assignees: JECHO LABORATORIES, INC., Frederick, MD (US); JECHO INSTITUTE, CO., LTD., Shanghai (CN)

( * ) Notice: Subject to any disclaimer, the term of this patent is extended or adjusted under 35 U.S.C. 154(b) by 894 days.

(21) Appl. No.: 17/280,636

(22) PCT Filed: Sep. 27, 2019

(86) PCT No.: PCT/CN2019/108588
§ 371 (c)(1),
(2) Date: Mar. 26, 2021

(87) PCT Pub. No.: WO2020/063880
PCT Pub. Date: Apr. 2, 2020

(65) Prior Publication Data
US 2022/0282231 A1    Sep. 8, 2022

(30) Foreign Application Priority Data
Sep. 30, 2018    (CN) .......................... 201811162604.0

(51) Int. Cl.
*C12N 9/14* (2006.01)
*A61P 35/00* (2006.01)
(Continued)

(52) U.S. Cl.
CPC ................ *C12N 9/14* (2013.01); *A61P 35/00* (2018.01); *C07K 14/21* (2013.01); *C12N 15/11* (2013.01); *C07K 2319/55* (2013.01)

(58) Field of Classification Search
CPC    C12N 9/14; C12N 15/11; A61P 35/00; C07K 14/21
See application file for complete search history.

(56) References Cited

U.S. PATENT DOCUMENTS 7,405,276 B2    7/2008    Himawan
8,491,908 B2    7/2013    Kanazaki et al.
(Continued)

FOREIGN PATENT DOCUMENTS

CN    104053779 A    9/2014
CN    105142675 A    12/2015
(Continued)

OTHER PUBLICATIONS

Han et al (Sci Rep. Aug. 21, 2017;7(1):8360) (Year: 2017).*
(Continued)

*Primary Examiner* — Thomas J. Visone
*Assistant Examiner* — Georgiana C Reglas
(74) *Attorney, Agent, or Firm* — Merchant & Gould P.C.; Daniel J. Pereira

(57)    ABSTRACT

A polypeptide composition, and methods of making the same, may include a first polypeptide and a second polypeptide, wherein the first polypeptide comprise a first toxin fragment and a first intein fragment, the second polypeptide comprise a second toxin fragment and a second intein fragment, the first polypeptide is different from the second polypeptide; the first toxin fragment and the second toxin fragment are non-biotoxic; the first polypeptide and the second polypeptide may make the first toxin fragment and the second toxin fragment into biotoxic toxins by an inter-
(Continued)

action of the first intein fragment and the second intein fragment. Kits may include such first and second polypeptides, and such compositions and kits may be used in treating tumors.

19 Claims, 8 Drawing Sheets

Specification includes a Sequence Listing.

(51) Int. Cl.
*C07K 14/21* (2006.01)
*C12N 15/11* (2006.01)

(56) References Cited

U.S. PATENT DOCUMENTS

| 8,932,586 | B2 * | 1/2015 | Jones | C12N 9/1077 |
|---|---|---|---|---|
| | | | | 435/193 |
| 9,872,923 | B2 | 1/2018 | Grawunder et al. | |
| 10,100,080 | B2 | 10/2018 | Pallisse Bergwerf et al. | |
| 2010/0047179 | A1 | 2/2010 | Demidov et al. | |
| 2011/0172391 | A1 | 7/2011 | Liu et al. | |
| 2011/0294987 | A1 | 12/2011 | Kanazaki et al. | |
| 2016/0102332 | A1 | 4/2016 | Collier et al. | |
| 2019/0262461 | A1 | 8/2019 | Grawunder et al. | |

FOREIGN PATENT DOCUMENTS

| CN | 105925596 A | 9/2016 |
|---|---|---|
| CN | 106397598 A | 2/2017 |
| WO | WO 02/46208 A2 | 6/2002 |
| WO | WO 2008/133709 A2 | 11/2008 |
| WO | WO 2009/132455 A1 | 11/2009 |
| WO | WO 2014/088928 A1 | 6/2014 |
| WO | WO 2017/143839 A1 | 8/2017 |
| WO | WO 2019/165444 A1 | 8/2019 |

OTHER PUBLICATIONS

Allahyari et al (Immunotoxin: A new tool for cancer therapy. Tumour Biol. Feb. 2017;39(2):1010428317692226) (Year: 2017).*
Chinese Office Action issued Jun. 8, 2022 in Chinese Patent Application No. 201980064610.9, 7 pages.
Extended European Search Report issued Jun. 10, 2022 in European Patent Application No. 19867591.0, 11 pages.
Alford, S.C., et al., "Conditional Toxin Splicing Using a Split Intein System", Split Inteins:Methods and Protocols, vol. 1495, Oct. 7, 2016, XP009512348, pp. 194-216.
Shi, C., et al., "A General Purification Platform for Toxic proteins Based on Intein trans-splicing", Applied Microbiology and Biotechnology, Nov. 1, 2014. vol. 98, No. 22, XP055291431, pp. 9425-9435.
Topilina, N., et al., "Recent advances in in vivo applications of intein-mediated protein splicing", Mobile DNA, vol. 5, No. 1, Feb. 4, 2014, XP021176410, pp. 1-14.
Akbari, B., et al., "Immunotoxins in cancer therapy: Review and update", International Reviews of Immunology, vol. 36, No. 4, Jan. 2017, XP009514160, pp. 207-219.
International Search Report issued on Dec. 30, 2019 in PCT/CN2019/108588 filed on Sep. 27, 2019, 6 pages.
Wang, J. et al., "Reduction of non-specific toxicity of immunotoxin by intein mediated reconstitution on target cells," International Immunopharmacology, vol. 66, 2019, pp. 288-295.
Alford, S. C. et al., "Conditional Toxin Splicing Using a Split Intein System," Split Inteins: Methods and Protocols, Methods in Molecular Biology, vol. 1495, Chapter 13, 2016, pp. 197-216.
Pirzer, T. et al., "Generation of Potent Anti-HER1/2 Immunotoxins by Protein Ligation Using Split Inteins," ACS Chemical Biology, vol. 13, 2018, pp. 2058-2066.

* cited by examiner

First polypeptide | Translocation region | First fragment of the toxic active region | First intein fragment Second polypeptide | Second intein fragment | Second fragment of the toxic active region

Fig. 14

First polypeptide | First intein fragment | First fragment of the toxic active region | Translocation region Second polypeptide | Second fragment of the toxic active region | Second intein fragment

Fig. 15

POLYPEPTIDE COMPOSITION

CROSS-REFERENCE TO RELATED APPLICATIONS

The present application is a National Stage Application and claims priority under 35 U.S.C. § 371 to Patent Cooperation Treaty application PCT/CN2019/108588, filed Sep. 27, 2019, which claims the benefit of Chinese patent application CN 201811162604.0, filed Sep. 30, 2018. Priority is claimed to these applications, the entire disclosure of each of which, to the extent allowed, is incorporated by reference herein.

TECHNICAL FIELD

The present application relates to the field of immunotherapy, especially relates to a polypeptide composition, and further relates to a kit including the polypeptide composition, and use of the polypeptide composition for treating tumors.

In accordance with 37 CFR § 1.52(e)(5) and with 37 CFR § 1.831, the specification makes reference to a Sequence Listing submitted electronically as a .txt file named "535195US_ST25.txt". The .txt file was generated on Dec. 2, 2021 and is 48,000 bytes in size. The entire contents of the Sequence Listing are hereby incorporated by reference.

BACKGROUND

Immunotoxin is a therapeutic chimeric protein composed of a cell targeting portion and a toxin portion, which has a function of specifically targeting and killing pathological cells, and may be prepared by means of chemical coupling or gene recombination.

Studies have shown that malignant tumors may overexpress many tumor-associated antigens, providing corresponding targets for targeted therapy. The targeted portion of immunotoxin allows targeted delivery of toxin drugs to tumor cells, thereby improving the specific killing effect and reducing the toxicity to normal cells. The cell targeting portion may be an antibody. The cell targeting portion may specifically target tumor cells, and is responsible for the specific binding of cells and endocytosis. The toxin portion enters into the cytoplasm through the cell targeting portion, interferes with the cell process in the cytoplasm so as to directly induce cell death, or modifies the cell membrane and induces apoptotic proteins so as to indirectly cause cell death, or functions to inhibit the growth of tumor cells and lead to cell death.

However, normal tissues also express tumor-associated antigens to varying extents. Therefore, immunotoxins still have non-specific toxicity to normal tissue cells and thus lead to drug safety problems.

SUMMARY OF THE INVENTION

The present application provides a polypeptide composition including a first polypeptide and a second polypeptide. The present application further provides a method of preparing the composition, a kit including the first polypeptide and the second polypeptide, and use and method of the composition and the kit in the treatment of tumors.

In an aspect, the present application provides a composition including a first polypeptide and a second polypeptide, wherein the first polypeptide includes the first toxin fragment and the first intein fragment, the second polypeptide includes the second toxin fragment and the second intein fragment; wherein the first polypeptide is different from the second polypeptide; the first toxin fragment and the second toxin fragment are non-biotoxic; and the first polypeptide and the second polypeptide may make the first toxin fragment and the second toxin fragment to form a biotoxic toxin by means of the interaction between the first intein fragment and the second intein fragment. In some embodiments, the first toxin fragment is different from the second toxin fragment. In some embodiments, the first toxin fragment and the second toxin fragment are derived from the same toxin.

In some embodiments, the first toxin fragment includes a first fragment of a toxic active region of the toxin, the second toxin fragment includes a second fragment of a toxic active region of the toxin, and the first fragment of the toxic active region and the second fragment of the toxic active region constitute an intact toxic active region of the toxin. In some embodiments, the second toxin fragment does not include a translocation region of the toxin or a fragment thereof. In some embodiments, the first toxin fragment further includes a translocation region of the toxin or a fragment thereof. In some embodiments, the first toxin fragment does not include an intact toxic active region of the toxin. In some embodiments, the second toxin fragment does not include an intact toxic active region of the toxin.

In some embodiments, the toxin is selected from the group consisting of bacterial toxin, human-derived toxin and phytotoxins. In some embodiments, the toxin is selected from the group consisting of *Pseudomonas aeruginosa* exotoxin and diphtheria toxin. In some embodiments, the toxin is selected from the group consisting of ricin, saporin and gelonin. In some embodiments, the toxin is the truncated form of *Pseudomonas aeruginosa* exotoxin PE38, which includes an amino acid sequence as shown in any one of SEQ ID NO: 1 and SEQ ID NO: 16.

In some embodiments, the first intein fragment is different from the second intein fragment. In some embodiments, the first intein fragment and the second intein fragment are derived from the same intein. In some embodiments, the intein is a split intein. In some embodiments, the split intein is selected from the group consisting of SsP DnaB, Ssp DnaE and Npu DnaE.

In some embodiments, in the first polypeptide, the C-terminal of the first toxin fragment is directly or indirectly linked to the N-terminal of the first intein fragment. In some embodiments, the amino acid residue of the C-terminal of the first toxin fragment is derived from a random coil region of the toxin. In some embodiments, in the second polypeptide, the N-terminal of the second toxin fragment is directly or indirectly linked to the C-terminal of the second intein fragment. In some embodiments, the amino acid residue of the N-terminal of the second toxin fragment is derived from a random coil region of the toxin. In some embodiments, the amino acid residues at sites 1-3 of the N-terminal of the second toxin fragment are sequentially CFN.

In some embodiments, the first intein fragment comprises an amino acid sequence as set forth in SEQ ID NO: 2. In some embodiments, the second intein fragment comprises an amino acid sequence as set forth in SEQ ID NO: 3. In some embodiments, the first toxin fragment comprises an amino acid sequence as set forth in SEQ ID NO: 4. In some embodiments, the second toxin fragment comprises an amino acid sequence as set forth in SEQ ID NO: 5. In some embodiments, the first polypeptide comprises an amino acid sequence as set forth in SEQ ID NO: 6. In some embodiments, the second polypeptide comprises an amino acid sequence as set forth in any one of SEQ ID NO: 7 and SEQ ID NO:15.

In some embodiments, in the first polypeptide, the N-terminal of the first toxin fragment is directly or indirectly linked to the C-terminal of the first intein fragment. In some embodiments, an amino acid residue of the N-terminal of the first toxin fragment is derived from a random coil region of the toxin. In some embodiments, in the second polypeptide, the C-terminal of the second toxin fragment is directly or indirectly linked to the N-terminal of the second intein fragment. In some embodiments, an amino acid residue of the C-terminal of the second toxin fragment is derived from a random coil region of the toxin. In some embodiments, the amino acid residues at sites 1-3 of the N-terminal of the first toxin fragment are sequentially CFN.

In some embodiments, the first intein fragment comprises an N-terminal protein region of the split intein; and the second intein fragment comprises a C-terminal protein region of the split intein.

In some embodiments, the first intein fragment comprises a C-terminal protein region of the split intein; and the second intein fragment comprises an N-terminal protein region of the split intein.

In some embodiments, the N-terminal protein region is the N-terminal protein region of Npu DnaE.

In some embodiments, the C-terminal protein region is the C-terminal protein region of Npu DnaE.

In some embodiments, the interaction between the first intein fragment and the second intein fragment comprises a protein trans-splicing of the first intein fragment and the second intein fragment.

In some embodiments, the first polypeptide and/or the second polypeptide further include(s) a targeting portion, and the targeting portion targets a tumor-specific antigen. In some embodiments, the first polypeptide comprises a first targeting portion, and the first targeting portion is located at the N-terminal of the first toxin fragment. In some embodiments, the second polypeptide comprises a second targeting portion, and the second targeting portion is located at the N-terminal of the second toxin fragment.

In some embodiments, the tumor-specific antigen is selected from the group consisting of HER2, PD-L1, EGFR, mesothelin and Lewis Y. In some embodiments, the first targeting portion and/or the second targeting portion comprise(s) antibody or an antigen-binding fragment thereof or a variant thereof. In some embodiments, the antibody is selected from the group consisting of monoclonal antibody, single-chain antibody, chimeric antibody, humanized antibody and fully human antibody. In some embodiments, the antigen-binding fragment is selected from the group consisting of Fab, Fab', F(ab)$_2$, dAb, isolated complementary determinant region CDR, Fv and scFv.

In some embodiments, the variant of the antibody or the antigen-binding fragment thereof is selected from the group consisting of: a) a protein or polypeptide obtained by substituting, deleting or adding one or more amino acids in the antibody or the antigen-binding fragment thereof; and b) a protein or polypeptide having at least 90% sequence identity with the antibody or the antigen-binding fragment thereof.

In some embodiments, the first targeting portion and/or the second targeting portion are/is ScFv. In some embodiments, the targeting portion comprises an amino acid sequence as set forth in SEQ ID NO: 8.

In another aspect, the present application provides a method of preparing a composition, which comprises the following steps: 1) providing the first polypeptide; 2) providing the second polypeptide; and 3) mixing the first polypeptide with the second polypeptide to obtain the composition. In some embodiments, in the preparation method, the molar ratio of the first polypeptide to the second polypeptide in the composition is 10:1-1:10.

In some embodiments, the preparation method further comprises adding a reducing agent. In some embodiments, in the preparation method, the reducing agent is selected from the group consisting of DTT and β-mercaptoethanol. In some embodiments, in the preparation method, the concentration of the reducing agent is 0.001-10000 nM.

In some embodiments, in the preparation method, the reducing agent is added simultaneously with or after the mixing. In some embodiments, the preparation method further comprises incubating the composition after adding the reducing agent. In some embodiments, in the preparation method, the incubation is performed at a temperature of 1° C.-50° C. In some embodiments, in the preparation method, the incubation is performed for a period of 2-120 minutes.

In another aspect, the present application provides a vector, which comprises a nucleic acid encoding the first polypeptide, and/or comprising a nucleic acid encoding the second polypeptide.

In another aspect, the present application provides a cell expressing the first polypeptide and/or expressing the second polypeptide.

In another aspect, the present application provides a kit, which comprises 1) the first polypeptide; and 2) the second polypeptide. In some embodiments, in the kit, the first polypeptide and the second polypeptide are not mixed with each other in the kit. In some embodiments, in the kit, the first polypeptide and the second polypeptide are located in different containers.

In some embodiments, in the kit, the kit further comprises a reducing agent. In some embodiments, in the kit, the reducing agent is selected from the group consisting of DTT and β-mercaptoethanol. In some embodiments, in the kit, the reducing agent is contained in a separate container.

In some embodiments, the kit comprises the composition.

In another aspect, the present application provides use of the composition, the kit, the vector, or the cell in preparation of a medicament for treating disease, wherein the disease comprises tumor. In some embodiments, the tumor is selected from the group consisting of breast cancer, melanoma, ovarian cancer, colon cancer, mesothelioma, adenoma, pancreatic cancer and bladder cancer.

In another aspect, the present application provides the composition, the kit, the vector, or the cell for treating tumor.

In another aspect, the present application provides a method of treating tumor, comprising administering the composition, the kit, the vector, or the cells.

Persons skilled in the art may readily recognize other aspects and advantages of the present disclosure from the following detailed description. The following detailed description only shows and describes exemplary embodiments of the present disclosure. As those skilled in the art will appreciate, the present disclosure enables persons skilled in the art to modify the disclosed specific embodiments without departing from the spirit and scope of the invention involved in the present application. Correspondingly, the drawings of the present application and the description in the specification are merely exemplary, rather than limitative.

BRIEF DESCRIPTION OF THE DRAWINGS

The specific features of the invention involved in the present application are shown in the appended claims. By reference to the exemplary embodiments and drawings as detailedly described hereinafter, the features and advantages of the invention involved in the present application may be better understood. The drawings are briefly described as follows:

FIG. 14 shows the structures of the first and the second polypeptides in the composition;

FIG. 15 shows the structures of the first and the second polypeptides in the composition.

DETAILED DESCRIPTION OF THE EMBODIMENTS

Figure 1:
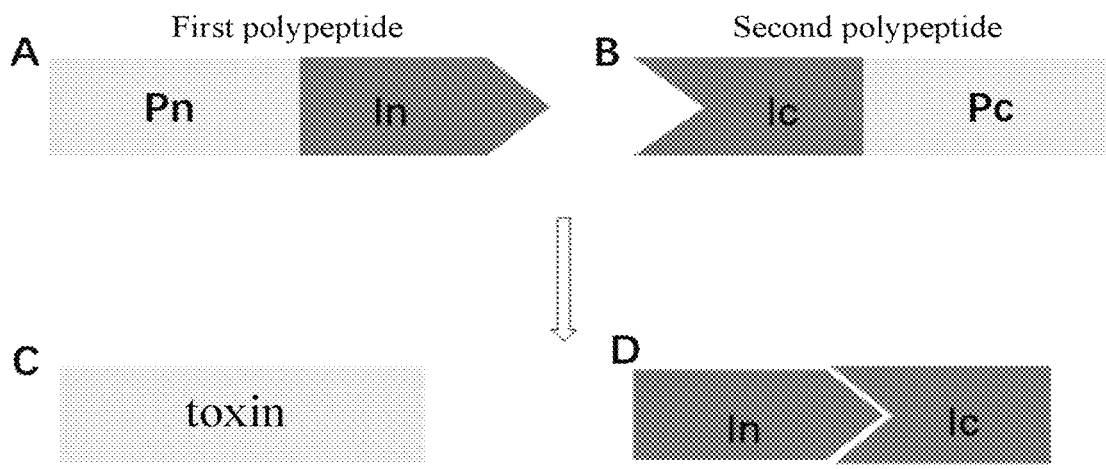
FIG. 1 shows the structure of the composition of the present application.

Hereinafter the embodiments of the invention of the present application are described by specific examples. Those skilled in the art may easily understand other advantages and effects of the invention of the present application from the disclosure in the present description.

In the present application, the term "immunotoxin (recombinant immunotoxin, RIT)" generally refers to a therapeutic chimeric protein composed of a cell-targeting portion and a toxin portion that has a function of specifically targeting pathologic cells and killing the pathological cells. By the binding between the cell-targeting portion and the target cell surface specific receptor antigen, the cell-targeting portion serves to specifically bind the target cells and is endocytosed by the target cells. The toxin portion may enter the cytoplasm by the cell-targeting portion, interfere with the cellular process in the cytoplasm to directly induce the cell death; or the toxin portion may modify the cell membrane, and induce apoptosis protein to indirectly cause cell death, thereby functioning to inhibit the growth of pathological cells and leading to the cell death.

In the present application, the term "toxin" generally refers to any substance that is harmful to the growth and proliferation of cells and may function to reduce, inhibit or destroy cells or malignant tumors. These substances are usually proteins that interfere with the action of other macromolecules in the organism. According to the source, toxin may comprise bacterial toxin, phytotoxin and human-derived toxin. For example, the bacterial toxin may comprise *Pseudomonas aeruginosa* exotoxins (PE) and diphtherin (DT), and the phytotoxins may comprise ricin and abrin. In some cases, toxins may function by inhibiting the protein synthesis via enzymatic hydrolysis. Generally, toxins may comprise the following functional regions: cell binding region, translocation region and toxic active region.

In the present application, the term "cell-binding region" generally refers to a functional region of toxin that may enrich the toxin on the target cell surface.

In the present application, the term "translocation region" generally refers to a functional region of toxin that may allow the toxin to reach the cytoplasmic region across the membrane.

In the present application, the term "toxic active region" generally refers to a functional region of toxin that may inactivate some important cell processes and kill the cell.

In the present application, the term "polypeptide" generally refers to a compound formed from $\alpha$-amino acids linked via a peptide bond, which is also an intermediate product of protein hydrolysis. A compound formed by dehydration and condensation of two amino acid molecules is called dipeptide. Similarly, there are tripeptide, tetrapeptide, pentapeptide and the like. Generally, a compound formed by dehydration and condensation of three or more amino acid molecules may be called polypeptide.

In the present application, the term "biotoxicity" generally refers to cytotoxicity that may be a simple cell killing event caused by cells or chemicals, independent of the cell death mechanism of apoptosis or necrosis.

In the present application, the term "antibody" generally refers to a polypeptide molecule that may specifically recognize and/or neutralize a specific antigen. The basic four-chain antibody unit is a heterotetrametric glycoprotein, which is composed of two identical light chains and two identical heavy chains. In the case of IgG, each L chain is linked to an H chain via a covalent disulfide bond, while two H chains are linked to each other via one or more disulfide bonds, wherein the number of the disulfide bonds depends on the isotypes of H chains. Each H chain and each L chain further have regularly-spaced intrachain disulfide bonds. Each H chain has a variable domain (VH) at the N-terminal, followed by three (for each $\alpha$ and $\gamma$ chain) or four (for $\mu$ and $\epsilon$ isotypes) constant domains (CH).

In the present application, the term "antigen-binding fragment" generally refers to a portion of an intact antibody. For example, the antigen-binding fragment may be an antigen binding region and/or a variable region of an intact antibody. The antigen-binding fragment may be obtained by chemical and/or genetic engineering methods. The chemical method is to generate an antigen-binding fragment by cleaving the disulfide bond in the hinge region, or to produce the antigen-binding fragment by using a protease, including pepsin and papain to digest the antibody. The genetic engineering method refers to process and reassemble the genes encoding antibodies according to different requirements by use of recombinant DNA and protein engineering techniques, and transfect the suitable recipient cells to express antibody molecules.

In the present application, the term "intein" generally refers to an insertion sequence located in the host protein. The intein gene is not an independent gene, and may be replicated and transcribed only when it is inserted into an extein gene. It may be excised from the precursor protein, and the exteins at both sides may be linked to form a mature protein. The nucleotide sequence corresponding to the intein is inserted into the nucleic acid sequence corresponding to the host protein, exists in the same open reading frame with the host protein gene, and is transcribed and translated synchronously with the host protein gene. After being translated to form the protein precursor, the intein is excised from the host protein, so that a mature active protein is formed. According to the existing form of inteins, they may be divided into integral inteins and split inteins. The two splicing regions of the integral inteins co-exist in the same polypeptide fragment. The two splicing regions of the split inteins are split into two or more fragments, and exist in different polypeptide fragments, and thus the split inteins may also be called isolated inteins.

In the present application, the term "protein trans-splicing" generally refers to a protein splicing reaction mediated by a split intein. In this type of splicing process, firstly the N-terminal fragment (In) and the C-terminal fragment (Ic) of the split intein recognize and bind to each other via a non-covalent bond. After binding, the structure thereof is correctly folded, and the split intein which reconstructs an active center completes the protein splicing reaction according to the typical protein splicing pathway, to link the protein exteins at both sides with a naturally occurring peptide bond.

In the present application, the term "antigen" generally refers to a substance that may induce immune response in an organism, that is, a substance that may be specifically recognized and bound by a T/B lymphocyte surface antigen receptor (TCR/BCR) to activate, proliferate, and differentiate the T/B cells to produce immune response products (sensitized lymphocytes or antibodies), and may specifically bind to corresponding products in vivo and in vitro. Thus, the antigenic substances have two important characteristics: immunogenicity and immunoreactivity. Immunogenicity refers to the ability of the antigen to induce the organism to produce specific immune response and produce antibodies and/or sensitized lymphocytes; and immunoreactivity refers to the ability to react specifically with corresponding immune effectors (antibodies or sensitized lymphocytes) in vivo and in vitro.

In the present application, the term "tumor-specific antigen" generally refers to a new antigen that is present on the surface of certain tumor cells, but almost absent on normal cells, which is also called specific tumor antigen.

In the present application, the term "tumor" generally refers to neogrowths formed by the clonal abnormal proliferation of a certain cell in local tissue that loses the normal growth regulation at the gene level under the action of various carcinogenic factors. It is also called neoplasm because such neogrowth mostly presents occupying massive bumps.

In the present application, the term "monoclonal antibody" generally refers to a population of substantially homogeneous antibodies. That is, various antibodies contained in the population are the same except for possible naturally occurring mutations in a minor amount. The monoclonal antibody is highly specific and directly targets a single antigenic site. Moreover, in contrast to the polyclonal antibody preparations including different antibodies targeting different determinants (epitopes), each monoclonal antibody targets a single determinant on an antigen. The modifier "monoclonal" is not interpreted as that the antibody needs to be produced by any special method. For example, the monoclonal antibody may be prepared by hybridoma technique or produced in bacteria, eukaryotic animal or plant cells by using recombinant DNA methods. The monoclonal antibodies may also be obtained from a phage antibody library by using the technology described in, e.g., Clarkson et al., Nature, 352:624-628 (1991) and Marks et al., Mol. Biol, 222:581-597 (1991).

In the present application, the term "single-chain antibody (scFv)" generally refers to a molecule formed by the heavy chain variable region and the light chain variable region of the antibody via a short peptide linker.

In the present application, the term "chimeric antibody" generally refers to an antibody in which a portion of the amino acid sequence of each heavy chain or light chain is homologous with the corresponding amino acid sequence in the antibody from a specific species or belongs to a specific category, while the rest of the chain is homologous with the corresponding sequence in another species. For example, the variable regions of light chain and heavy chain are derived from the variable regions of antibodies from one animal species (e.g., mice, rats, etc.), while the constant regions are homologous with the antibody sequences from another species (e.g., human). For example, in order to obtain chimeric antibodies, non-human B cells or hybridoma cells may be used to produce variable regions, while the constant regions combined therewith are derived from human. The variable regions have the advantage of easy preparation, and their specificity is not affected by the source of the constant region combined therewith. At the same time, since the constant region of the chimeric antibody may be derived from human, the possibility of the chimeric antibody inducing an immune response during injection is lower than that of an antibody including the constant region derived from non-human source.

In the present application, the term "humanized antibody" generally refers to a modified antibody in which the immunogenicity of antibodies, immunoglobulin binding proteins and polypeptides derived from non-human species (such as mice or rats) to human body is reduced by genetic engineering technology, while the antigen binding characteristic of the original antibody is still maintained. For example, CDR transplantation (Jones et al., Nature 321:522 (1986)) and its variants, including the technical means like "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312) may be used to humanize the binding domains derived from non-human source. If other regions, such as, hinge regions or constant domains, are also derived from non-human sources, these regions may also be humanized.

In the present application, the term "fully human antibody" generally refers to an antibody that the whole antibody (including the constant regions, CH regions, and CL regions of the antibody) is encoded by genes derived from human. Fully human antibodies may greatly reduce the immune side reactions caused by heterologous antibody to human body.

In the present application, the term "vector" generally refers to a nucleic acid molecule capable of replicating itself in a suitable host, which transfers the inserted nucleic acid molecule into the host cell and/or between the host cells. The vector may comprise those mainly for inserting DNAs or RNAs into cells, those mainly for replicating DNAs or RNAs, and those mainly for expression of DNA or RNA transcription and/or translation. The vector may further comprise those having a plurality of the above-described functions. The vector may be a polynucleotide that may be transcribed and translated to a polypeptide when introduced into a suitable host cell. Generally, the vector may produce the anticipated expression product by culturing a suitable cell including the vector.

In the present application, the term "cell" generally refers to individual cells, cell lines, or cell culture that may comprise or have comprised a plasmid or vector comprising the nucleic acid molecule of the present application, or may express the polypeptide or polypeptide fragment of the present application. The cell may comprise a progeny cell of a single host cell. Due to natural, accidental, or intentional mutations, the progeny cell may not be necessarily the same as the original parent cells in morphology or genome, as long as they may express the polypeptide or polypeptide fragment of the present application. The cell may be obtained by in vitro transfecting cells by using the vector of the present application. The cell may be prokaryotic cells (e.g., *E. coli*), or may be eukaryotic cells.

In the present application, the term "identity" generally refers to the percentage of the number of the same amino acid residues in the number of all the amino acid residues by comparing a candidate sequence with a specific peptide or polypeptide sequence.

In the present application, the term "comprise/including" generally refers to the meaning of comprise, including, containing, or have. In some cases, it may also have the meaning of "being" or "consisting of".

Composition and Preparation Method Thereof

In an aspect, the present application provides a composition that may be a polypeptide composition. The composition may comprise a first polypeptide and a second polypeptide, wherein the first polypeptide may comprise a first toxin fragment and a first intein fragment, the second polypeptide may comprise a second toxin fragment and a second intein fragment; wherein the first polypeptide may be different from the second polypeptide; the first toxin fragment and the second toxin fragment may both be non-biotoxic; and the first polypeptide and the second polypeptide may make the first toxic fragment and the second toxic fragment to form a biotoxic toxin by means of the interaction between the first intein fragment and the second intein fragment.

In the present application, the term "first toxin fragment" generally refers to a toxin fragment that is non-biotoxic and may not comprise an intact toxin. Under certain conditions, the first toxin fragment may combine with other toxin fragment(s) to form a toxin with biotoxicity.

In the present application, the term "second toxin fragment" generally refers to a toxin fragment that is non-biotoxic and may not comprise an intact toxin. Under certain conditions, the second toxin fragment may be combined with other toxin fragment(s) to form a toxin with biotoxicity. For example, under certain conditions, the second toxin fragment may be combined with the first toxin fragment to form a toxin with biotoxicity.

In the present application, the term "first intein fragment" generally refers to a partial fragment of an intein that may not comprise an intact intein fragment. Under certain conditions, the first intein fragment may interact with other intein fragment(s) to allow the first toxin fragment and the second toxin fragment to form a toxin with biotoxicity.

In the present application, the term "second intein fragment" generally refers to a partial fragment of an intein that may not comprise an intact intein fragment. Under certain conditions, the second intein fragment may interact with other intein fragment(s) to allow the first toxin fragment and the second toxin fragment to form a toxin with biotoxicity. For example, under certain conditions, the second intein fragment may interact with the first intein fragment to make the first toxin fragment and the second toxin fragment to form a toxin with biotoxicity.

In the present application, the term "first polypeptide" generally refers to a polypeptide non-biotoxic and comprising a first toxin fragment and a first intein fragment. Under certain conditions, the first intein fragment in the first polypeptide may interact with the intein fragment in other polypeptide(s) to make the first toxin fragment in the first polypeptide and the toxin fragment in other polypeptide(s) to form a toxin with biotoxicity.

In the present application, the term "second polypeptide" generally refers to a non-biotoxic polypeptide and comprising a second toxin fragment and a second intein fragment. Under certain conditions, the second intein fragment in the second polypeptide may interact with the intein fragment in another polypeptide to make the second toxin fragment in the second polypeptide and the toxin fragment in other polypeptide to form a toxin with biotoxicity. For example, under certain conditions, the second intein fragment in the second polypeptide may interact with the first intein fragment in the first polypeptide to make the second toxin fragment in the second polypeptide and the first toxin fragment in the first polypeptide to form a toxin with biotoxicity.

In the present application, the composition may comprise a first polypeptide and a second polypeptide, the first polypeptide may comprise the first toxin fragment and the first intein fragment, the second polypeptide may comprise the second toxin fragment and the second intein fragment, the amino acid sequences of the first polypeptide and the second polypeptide may be different. For instance, the amino acid sequences of the first polypeptide and the second polypeptide have an identify of less than 99%, less than 98%, less than 95%, 90%, less than 80%, less than 70%, less than 60%, less than 50%, less than 40%, less than 30%, less than 20%, less than 10% or less. Both the first toxin fragment and the second toxin fragment may be non-biotoxic, and both the first polypeptide and the second polypeptide may also be non-biotoxic. Under certain conditions, the first intein fragment and the second intein fragment may interact with each other to make the first toxin fragment and the second toxin fragment to form a toxin with biotoxicity.

In the present application, the first toxin fragment may be different from the second toxin fragment. In the present application, the amino acid sequences of the first toxin fragment and the second toxin fragment may be different. For example, the amino acid sequences of the first toxin fragment and the second toxin fragment may have an identity of less than 99%, less than 98%, less than 95%, 90%, less than 80%, less than 70%, less than 60%, less than 50%, less than 40%, less than 30%, less than 20%, less than 10% or less. In some cases, the first toxin fragment and the second toxin fragment may be derived from the same toxin. The first toxin fragment and the second toxin fragment may be intercepted from different sequence sites in the same toxin.

In the present application, the first toxin fragment may comprise a first fragment of the toxic active region of the toxin, the second toxin fragment may comprise a second fragment of the toxic active region of the toxin, and the first fragment of the toxic active region and the second fragment of the toxic active region constitute the intact toxic active region of the toxin.

In the present application, the term "first fragment of the toxic active region" generally refers to a partial fragment of the toxic active region of the toxin, the first fragment of the toxic active region does not comprise the intact toxin active region of the toxin. Under certain conditions, the first fragment of the toxic active region may be combined with the fragment of another toxic active region to form an intact toxic active region.

In the present application, the term "second fragment of the toxic active region" generally refers to a partial fragment of the toxic active region of the toxin, the second fragment of the toxic active region does not comprise the intact toxin active region of the toxin. Under certain conditions, the second fragment of the toxic active region may be combined with fragment of another toxic active region to form an intact toxic active region. For example, under certain conditions, the second fragment of the toxic active region may be combined with the first fragment of the toxic active region to form an intact toxic active region.

In the present application, the toxin may comprise a toxic active region. In the present application, the first toxin fragment may comprise a first fragment of the toxic active region of the toxin, the second toxin fragment may comprise a second fragment of the toxic active region of the same toxin, both the first toxin fragment and the second toxin fragment do not comprise the intact toxic active region of the toxin. Under certain conditions, the first fragment of the toxic active region and the second fragment of the toxic active region may constitute an intact toxic active region of the toxin.

In the present application, the toxin may further comprise a translocation region. In the present application, the second toxin fragment may not comprise the translocation region or its fragment of the toxin, the first toxin fragment may further comprise the translocation region or its fragment of the toxin. The second toxin fragment may not comprise an intact translocation region of the toxin, or the second toxin fragment may not comprise a translocation region fragment of the toxin. The first toxin fragment may further comprise the intact translocation region of the toxin, or the first toxin fragment may further comprise the translocation region fragment of the toxin. For example, the first toxin fragment may comprise the first fragment of the toxic active region of the toxin and the intact translocation region of the toxin, the second toxin fragment may comprise the second fragment of the toxic active region of the same toxin. For example, the first toxin fragment may comprise the first fragment of the toxic active region of the toxin and the translocation region fragment of the toxin, and the second toxin fragment may comprise the second fragment of the toxic active region of the same toxin.

In the present application, the toxin may be selected from the group consisting of bacterial toxin, human-derived toxin and phytotoxin. In the present application, the toxin may be bacterial toxin, human-derived toxin, phytotoxin or their combination. In the present application, the toxin may be selected from the group consisting of: *Pseudomonas aeruginosa* exotoxin and diphtherin. For example, the toxin may be *Pseudomonas aeruginosa* exotoxin, diphtherin or their combination. In the present application, the toxin may be selected from the group consisting of: ricin, saporin and gelonin. For example, the toxin may be ricin, saporin, gelonin or their combination.

In the present application, the toxin may be a truncated form of *Pseudomonas aeruginosa* exotoxin (PE) PE38. The truncated form PE38 may comprise an amino acid sequence as set forth in any one of SEQ ID NO:1 and SEQ ID NO: 16.

In the present application, the term "truncated form PE38" generally refers to a fragment of PE in which the cell binding region is truncated. The intact PE contains three functional regions, that is, a cell binding region (Ia region, 1-252 aa), a translocation region (II region, 253-364 aa) and a toxic active region (III region, 400-613 aa). The translocation region may allow the toxin to reach the functional region of the cytoplasmic region across the membrane. The toxic active region has a function of ADP ribosylation, which is the key functional region to inactivate the elongation factor eEF2 and kill cells. Due to the truncation of the cell binding region (Ia region, 1-252 aa) in truncated form PE38 of PE, the truncated form PE38 only comprises the translocation region (II region, 253-364 aa) and the toxic active region (III region, 400-613 aa).

In the present application, the first intein fragment may be different from the second intein fragment. The first and the second intein fragments may be derived from the same intein, and the intein may be a split intein. For example, the first intein fragment and the second intein fragment may have different amino acid sequences, e.g., the identity of amino acid sequences of the first intein fragment and the second intein fragment is less than 99%, less than 98%, less than 95%, 90%, less than 80%, less than 70%, less than 60%, less than 50%, less than 40%, less than 30%, less than 20%, less than 10%, or less. The first intein fragment and the second intein fragment may be parts of fragments of the same split intein, and the first intein fragment and the second intein fragment may be derived from different sequence sites of the same split intein.

In the present application, the split intein may be selected from the group consisting of: SsP DnaB, Ssp DnaE and Npu DnaE. For example, the split intein may be SsP DnaB, Ssp DnaE, Npu DnaE or their combination.

As shown in FIG. 14, in the present application, in the first polypeptide, the C-terminal of the first toxin fragment may be directly or indirectly linked to the N-terminal of the first intein fragment, the amino acid residues at the C-terminal of the first toxin fragment may be derived from the random coil region of the toxin. In the second polypeptide, the N-terminal of the second toxin fragment may be directly or indirectly linked to the C-terminal of the second intein fragment, and the amino acid residues at the N-terminal of the second toxin fragment are derived from the random coil region of the toxin.

In the present application, the C-terminal and the N-terminal are two tail ends of the polypeptide chain. The term "amino acid residue at the C-terminal" generally refers to the amino acid residue which is located at the tail end of the polypeptide and may carry a free alpha-carboxyl group.

In the present application, the term "amino acid residue at the N-terminal" generally refers to the amino acid residue which is located at the tail end of the polypeptide and may carry an alpha-amino group.

In the present application, the term "random coil region" generally refers to a region with relatively irregular arrangement of rings or coil structures in the peptide chain. Random coil is a common secondary structure of proteins except α-helix, β-fold and β-turn.

For instance, the toxin is cleaved in the random coil region to give the first toxin fragment and the second toxin fragment, while the cleaving site in the random coil region corresponds to the C-terminal of the first toxin fragment and the N-terminal of the second toxin fragment.

In the first polypeptide, the C-terminal of the first toxin fragment and the N-terminal of the first intein fragment may be directly linked to each other, or may be indirectly linked via a linker or other peptide chain; in the second polypeptide, the N-terminal of the second toxin fragment and the C-terminal of the second intein fragment may be directly linked, or may be indirectly linked via other peptide chain.

In the present application, the amino acid residues at sites 1-3 of the N-terminal of the second toxin fragment may be sequentially CFN. In the present application, the amino acid residue at site 1 of the N-terminal of the second toxin fragment may be cysteine (C), the amino acid residue at site 2 of the N-terminal of the second toxin fragment may be phenylalanine (F), and the amino acid residue at site 3 of the N-terminal of the second toxin fragment may be aspartic acid (N).

In the present application, the first intein fragment may comprise the N-terminal protein region of the split intein; and the second intein fragment comprises the C-terminal protein region of the split intein.

In the present application, the term "N-terminal protein region" generally refers to a region adjacent to the N-terminal in the polypeptide chain. In some cases, the N-terminal protein region of the split intein may be the N-terminal protein region of Npu DnaE.

In the present application, the term "C-terminal protein region" generally refers to a region adjacent to the C-terminal in the polypeptide chain. In some cases, the C-terminal protein region of the split intein may be the C-terminal protein region of Npu DnaE.

As shown in FIG. 14, in the present application, the composition may comprise a first polypeptide and a second polypeptide, wherein the first polypeptide may comprise a first toxin fragment and a first intein fragment, the second polypeptide may comprise a second toxin fragment and a second intein fragment. The first toxin fragment may comprise a first fragment of the toxic active region and a translocation region of the toxin, the second toxin fragment may comprise the second fragment of the toxic active region of the toxin. From the N-terminal to the C-terminal, the first polypeptide may sequentially comprise the translocation region of the toxin, the first fragment of the toxic active region of the toxin and the first intein fragment. The translocation region of toxin, the first fragment of the toxic active region of the toxin, and the first intein fragment may be directly or indirectly linked to each other. From the N-terminal to the C-terminal, the second polypeptide may sequentially comprise the second intein fragment and the second fragment of the toxic active region of the toxin, wherein the second intein fragment and the second fragment of the toxic active region of the toxin may be directly or indirectly linked to each other. Of those, three amino acid residues at the N-terminal of the second toxin fragment may be subject to site-specific mutagenesis, so that the amino acid residues at sites 1-3 of the N-terminal are CFN in sequence.

In the present application, as shown in FIG. 1, the composition may comprise a first polypeptide and a second polypeptide. The first polypeptide (as shown in FIG. 1A) comprises a first toxin fragment (briefly, Pn) and a first intein fragment (briefly, In), the second polypeptide (as shown in FIG. 1B) comprises a second toxin fragment (briefly, Pc) and a second intein fragment (briefly, Ic). The N-terminal of In is fused to the C-terminal of Pn, and the N-terminal of Pc is fused to the C-terminal of Ic. To improve the trans-splicing efficiency of the split intein, the amino acid of the N-terminal of Pc undergoes site-specific mutagenesis, so that the amino acid residues at sites 1-3 of the N-terminal of Pc are sequentially CFN. When the composition is under reducing condition, for example, under a microenvironment of a tumor, In and Ic undergo an intein trans-splicing reaction (as shown in FIG. 1D), while Pn and Pc are linked to form a toxin with biotoxicity (as shown in FIG. 1C) that has killing effect on tumor cells.

In the present application, the toxin may be a truncated form of *Pseudomonas aeruginosa* exotoxin (PE) PE38, the split intein may be Npu DnaE. Npu DnaE may be truncated into a N-terminal protein region and a C-terminal protein region, wherein the N-terminal protein region is the N-terminal protein region of Npu DnaE, and the C-terminal protein region is the C-terminal protein region of Npu DnaE. The N-terminal protein region constitutes the first intein fragment, and the C-terminal protein region constitutes the second intein fragment. In the present application, the toxic active region of PE38 (III region, 400-613 aa) comprises a random coil region, an alpha-helix region, and a lamella region. In order to enable the first toxin fragment and the second toxin fragment to be connected and restore the original conformation after the trans-splicing reaction of the intein, the truncated form PE38 may be cleaved in the random coil region instead of in the alpha-helix region or the lamella region. By cleaving PE38 with Npu DnaE in the random coil region, obtain the first toxin fragment and the second toxin fragment. In the present application, to improve the trans-splicing reaction mediated by the split intein, the three amino acid residues at the N-terminal of the second toxin fragment may undergo site-specific mutagenesis, so that the amino acid residues at sites 1-3 of the N-terminal are sequentially CFN. Site-specific mutagenesis facilitates the interaction between the proteins of the first intein fragment and the second intein fragment, so that the C-terminal of the first toxin fragment and the N-terminal of the second toxin fragment are linked to form a toxin with biotoxicity, so that the composition has a killing effect on tumor cells.

In the present application, the composition comprises a first polypeptide and a second polypeptide. The first intein fragment may comprise an amino acid sequence as set forth in SEQ ID NO:2, and the second intein fragment may comprise an amino acid sequence as set forth in SEQ ID NO:3. The first toxin fragment may comprise an amino acid sequence as set forth in SEQ ID NO: 4, and the second toxin fragment may comprise an amino acid sequence as set forth in SEQ ID NO: 5. The first polypeptide may comprise an amino acid sequence as set forth in SEQ ID NO: 6, and the second polypeptide may comprise an amino acid sequence as set forth in any one of SEQ ID NO: 7 and SEQ ID NO: 15. In the present application, the reducibility of the tumor microenvironment may promote the protein trans-splicing reaction of the split intein, so that a protein trans-splicing occurs between the first intein fragment and the second intein fragment when the composition is on the surface of the tumor cell, and the first toxin fragment and the second toxin fragment may form a toxin with biotoxicity. By ingestion of the toxin, the tumor cells may function to kill the pathological cells.

As shown in FIG. 15, in the present application, in the first polypeptide, the N-terminal of the first toxin fragment may be directly or indirectly linked to the C-terminal of the first intein fragment, and the amino acid residues at the N-terminal of the first toxin fragment may be derived from the random coil region of the toxin. In the second polypeptide, the C-terminal of the second toxin fragment may be directly or indirectly linked to the N-terminal of the second intein fragment, and the amino acid residues at the C-terminal of the second toxin fragment are derived from the random coil region of the toxin. For example, the toxin is cleaved in the random coil region to give the first toxin fragment and the second toxin fragment, wherein the cleavage site in the random coil region corresponds to the N-terminal of the first toxin fragment and the C-terminal of the second toxin fragment, and the N-terminal of the first toxin fragment as obtained is directly or indirectly linked to the C-terminal of the first intein fragment, and the C-terminal of the second toxin fragment is directly or indirectly linked to the N-terminal of the second intein fragment.

In the present application, the amino acid residues at sites 1-3 of the N-terminal of the first toxin fragment are sequentially CFN. In the present application, the amino acid residue at site 1 of the N-terminal of the first toxin fragment may be cysteine (C), the amino acid residue at site 2 of the N-terminal of the first toxin fragment may be phenylalanine (F), and the amino acid residue at site 3 of the N-terminal of the first toxin fragment may be aspartic acid (N).

In the present application, the first intein fragment may comprise the C-terminal protein region of the split intein; and the second intein fragment may comprise the N-terminal protein region of the split intein. In the present application, in the first polypeptide, the N-terminal of the first toxin fragment may be directly or indirectly linked to the C-terminal of the first intein fragment; and in the second polypeptide, the C-terminal of the second toxin fragment may be directly or indirectly linked to the N-terminal of the second intein fragment.

As shown in FIG. 15, in the present application, the composition may comprise a first polypeptide and a second polypeptide, wherein the first polypeptide may comprise a first toxin fragment and a first intein fragment, and the second polypeptide may comprise a second toxin fragment and a second intein fragment. The first toxin fragment may comprise a first fragment of the toxic active region of the toxin and a translocation region. The second toxin fragment may comprise the second fragment of the toxic active region of the toxin. From the N-terminal to the C-terminal, the first polypeptide may sequentially comprise the first intein fragment, the first fragment of the toxic active region of the toxin and the translocation region of the toxin, and the first intein fragment, the first fragment of the toxic active region of the toxin and the translocation region of the toxin may be directly or indirectly linked. From the N-terminal to the C-terminal, the second polypeptide may sequentially comprise the second fragment of the toxic active region of the toxin and the second intein fragment, and the second fragment of the toxic active region of the toxin may be directly or indirectly linked to the second intein fragment. Of those, the three amino acid residues at the N-terminal of the first toxin fragment may be subject to site-specific mutagenesis, so that the amino acid residues at sites 1-3 of the N-terminal are CFN in sequence.

In the present application, the interaction between the first intein fragment and the second intein fragment may comprise the protein trans-splicing of the first intein fragment and the second intein fragment. In the present application, the protein trans-splicing reaction may be a protein splicing reaction mediated by a split intein.

In the present application, the first polypeptide and/or the second polypeptide may further comprise a targeting portion, and the targeting portion may target a tumor-specific antigen.

In the present application, the term "targeting portion" generally refers to a portion that specifically binds to and/or recognizes a tumor antigen. For example, the first polypeptide and the second polypeptide may respectively comprise a targeting portion that may specifically bind to and/or recognize a tumor-specific antigen. For example, the first polypeptide may comprise a targeting portion, and the targeting portion may specifically bind to and/or recognize a tumor-specific antigen. For example, the second polypeptide may comprise a targeting portion, and the targeting portion may specifically bind to and/or recognize a tumor-specific antigen. In the present application, the targeting portion may comprise an antibody or an antigen-binding fragment thereof or a variant thereof. The antibody may be selected from the group consisting of monoclonal antibody, single-chain antibody, chimeric antibody, humanized antibody and fully human antibody. In the present application, the tumor-specific antigen may be selected from the group consisting of HER2, PD-L1, EGFR, mesothelin and Lewis Y. For example, the targeting portion may be a monoclonal antibody that specifically binds to and/or recognizes HER2, PD-L1, EGFR, mesothelin and/or Lewis Y. For example, the targeting portion may be a single-chain antibody that specifically binds to and/or recognizes HER2, PD-L1, EGFR, mesothelin and/or Lewis Y For example, the targeting portion may be a chimeric antibody that specifically binds to and/or recognizes HER2, PD-L1, EGFR, mesothelin and/or Lewis Y For example, the targeting portion may be a humanized antibody that specifically binds to and/or recognizes HER2, PD-L1, EGFR, mesothelin and/or Lewis Y For example, the targeting portion may be a fully human antibody that specifically binds to and/or recognizes HER2, PD-L1, EGFR, mesothelin and/or Lewis Y.

In the present application, the antigen-binding fragment may be selected from the group consisting of Fab, Fab', F $(ab)_2$, dAb, isolated complementary determinant region CDR, Fv and scFv. For example, the targeting portion may be Fab, Fab', F $(ab)_2$, dAb, isolated complementary determinant region CDR, Fv, scFv or their combination.

In the present application, the term "Fab" generally refers to an antigen-binding fragment composed of an intact light chain, a heavy variable region (VH) and a first heavy chain constant domain (CH1). Each Fab fragment is monovalent relative to the antigen-binding, that is, it has a single antigen-binding site.

In the present application, the term "Fab'" generally refers to an antigen-binding fragment having several additional residues at the carboxyl terminal in the CH1 domain as compared with the Fab fragment. Fab' comprises one or more cysteines from the hinge region of the antibody.

In the present application, the term "F $(ab)_2$" generally refers to an antigen-binding fragment obtained by linking a pair of Fab fragments by cysteine.

In the present application, the term "Fv" generally refers to an antigen-binding fragment composed of VL and VH domains in a single arm of the antibody.

In the present application, the term "complementary determinant region CDR" generally refers to the three hypervariable regions (HVRs) of the light chain variable region (VL) and VH, and the hypervariable region is also called a complementary determinant region because this site may form precise complementation with the antigen determinant in the steric structure.

In the present application, the variants of the antibody or the antigen-binding fragment thereof may be a protein or polypeptide obtained by substituting, deleting or adding one or more (e.g., at least 1, at least 2, at least 3, at least 4, at least 5, at least 6, at least 7, at least 8, at least 9, at least 10, at least 15, at least 20, at least 30, or more) amino acids from the antibody or the antigen-binding fragment thereof.

In the present application, the variants of the antibody or the antigen-binding fragment thereof may be a protein or polypeptide having a sequence identity of at least 90% (e.g., at least 90%, at least 91%, at least 92%, at least 93%, at least 94%, at least 95%, at least 96%, at least 97%, at least 98%, at least 99%, or more) with the antibody or the antigen-binding fragment thereof.

In the present application, the first targeting portion and/or the second targeting portion may be ScFv. For example, the first targeting portion may be ScFv. For example, the second targeting portion may be ScFv. For example, the first targeting portion and the second targeting portion may be both ScFv. In the present application, the targeting portion may comprise an amino acid sequence as set forth in SEQ ID NO: 8.

In the present application, the first polypeptide may comprise a first targeting portion, and the first targeting portion may be located at the N-terminal of the first toxin fragment. For example, the first targeting portion may be directly linked to the amino acid residues at the N-terminal of the first toxin fragment; alternatively, the first targeting portion may be indirectly linked to the amino acid residues at the N-terminal of the first toxin fragment, wherein the indirect linking is linking by inserting a peptide linkage or inserting another peptide chain.

In the present application, the second polypeptide may comprise a second targeting portion and the second targeting portion may be located at the N-terminal of the second toxin fragment. For example, the second targeting portion may be directly linked to the amino acid residues at the N-terminal of the second toxin fragment; alternatively, the second targeting portion may be indirectly linked to the amino acid residues at the N-terminal of the second toxin fragment, wherein the indirect linking is linking by inserting a peptide linkage or inserting another peptide chain.

As shown in FIG. 14, in the present application, the composition may comprise a first polypeptide and a second polypeptide. From the N-terminal to the C-terminal, the first polypeptide may sequentially comprise the translocation region of the toxin, the first fragment of the toxic active region of the toxin and the first intein fragment, wherein the translocation region of the toxin, the first fragment of the toxic active region of the toxin and the first intein fragment may be directly or indirectly linked to each other. From the N-terminal to the C-terminal, the second polypeptide comprises sequentially the second intein fragment and the second fragment of the toxic active region of the toxin, wherein the second intein fragment and the second fragment of the toxic active region of the toxin may be linked directly or indirectly.

As for the composition shown in FIG. 14, in some cases, the first polypeptide may further comprise a first targeting portion, the second polypeptide may further comprise a second targeting portion. In some cases, from the N-terminal to the C-terminal, the first polypeptide may sequentially comprise the first targeting portion, the translocation region of the toxin, the first fragment of the toxic active region of the toxin and the first intein fragment, wherein the first targeting portion, the translocation region of the toxin, the first fragment of the toxic active region of the toxin and the first intein fragment may be directly or indirectly linked to each other; from the N-terminal to the C-terminal, the second polypeptide comprises sequentially the second intein fragment, the second fragment of the toxic active region of the toxin and the second targeting portion, and the second targeting portion, the second intein fragment and the second fragment of the toxic active region of the toxin may be directly or indirectly linked to each other. Under certain conditions, such as, when a reducing agent is added into the composition, or when the composition is located within the microenvironment of tumor, the first intein fragment interacts with the second intein fragment, so that the first targeting portion and the first toxin fragment (including the translocation region of the toxin and the first fragment of the toxic active region) of the first polypeptide and the second targeting portion and the second toxin fragment (including the second fragment of the toxic active region) of the second polypeptide are linked to each other to form an immunotoxin. From the N-terminal to the C-terminal, the immunotoxin sequentially comprises the first targeting portion, the translocation region of the toxin, the first fragment of the toxic active region, the second fragment of the toxic active region and the second targeting portion, and the first targeting portion, the translocation region of the toxin, the first fragment of the toxic active region, the second fragment of the toxic active region may be directly or indirectly linked to each other.

With respect to the composition as shown in FIG. 14, in some cases, the first polypeptide may further comprise a first targeting portion, and the second polypeptide may not comprise a targeting portion. From the N-terminal to the C-terminal, the first polypeptide sequentially comprises the first targeting portion, the translocation region of the toxin, the first fragment of the toxic active region of the toxin and the first intein fragment, wherein the first targeting portion, the translocation region of the toxin, the first fragment of the toxic active region of the toxin and the first intein fragment may be directly or indirectly linked to each other; from the N-terminal to the C-terminal, the second polypeptide sequentially comprises the second intein fragment and the second fragment of the toxic active region of the toxin, wherein the second intein fragment and the second fragment of the toxic active region of the toxin are directly or indirectly linked. Under certain conditions, such as, when a reducing agent is added into the composition, or when the composition is located in a tumor microenvironment, the first intein fragment interacts with the second intein fragment, so that the first targeting portion and the first toxin fragment (including the translocation region of the toxin, first fragment of the toxic active region of the toxin) of the first polypeptide and the second toxin fragment (including the second fragment of the toxic active region) of the second polypeptide are linked to form an immunotoxin. From the N-terminal to the C-terminal, the immunotoxin sequentially comprises the first targeting portion, the translocation region of the toxin, the first fragment of the toxic active region of the toxin and the second fragment of the toxic active region, wherein the first targeting portion, the translocation region of the toxin, the first fragment of the toxic active region of the toxin and the second fragment of the toxic active region are directly or indirectly linked.

As shown in FIG. 15, in the present application, the composition may comprise a first polypeptide and a second polypeptide. From the N-terminal to the C-terminal, the first polypeptide may sequentially comprise the first intein fragment, the first fragment of the toxic active region of the toxin and the translocation region of the toxin, the first intein fragment, the first fragment of the toxic active region of the toxin and the translocation region of the toxin may be directly or indirectly linked; from the N-terminal to the C-terminal, the second polypeptide may sequentially comprise the second fragment of the toxic active region of the toxin and the second intein fragment, the second fragment of the toxic active region of the toxin and the second intein fragment may be directly or indirectly linked.

With respect to the composition as shown in FIG. 15, in some cases, the first polypeptide may further comprise a first targeting portion, the second polypeptide may further comprise a second targeting portion. In some cases, from the N-terminal to the C-terminal, the first polypeptide may sequentially comprise the first intein fragment, the first fragment of the toxic active region of the toxin, the translocation region of the toxin and the first targeting portion, wherein the first targeting portion, the first intein fragment, the first fragment of the toxic active region of the toxin and the translocation region of the toxin may be directly or indirectly linked to each other; from the N-terminal to the C-terminal, the second polypeptide sequentially comprises the second targeting portion, the second fragment of the toxic active region of the toxin and the second intein fragment, wherein the second targeting portion, the second fragment of the toxic active region of the toxin and the second intein fragment may be directly or indirectly linked to each other. Under certain conditions, e.g., when a reducing agent is added into the composition, or when the composition is located in a tumor microenvironment, the first intein fragment interacts with the second intein fragment, so that the second targeting portion and the second toxin fragment (including the second fragment of the toxic active region) of the second polypeptide and the first targeting portion and the first toxin fragment (including the first fragment of the toxic active region of the toxin and the translocation region of the toxin) of the first polypeptide are linked to form an immunotoxin. From the N-terminal to the C-terminal, the immunotoxin sequentially comprises the second targeting portion, the second fragment of the toxic active region of the toxin, the first fragment of the toxic active region of the toxin, the translocation region of the toxin and the second targeting portion, wherein the second targeting portion, the second fragment of the toxic active region of the toxin, the first fragment of the toxic active region of the toxin and the translocation region of the toxin are directly or indirectly linked.

With respect to the composition as shown in FIG. 15, in some cases, the first polypeptide cannot comprise a targeting portion, and the second polypeptide may further comprise a second targeting portion. From the N-terminal to the C-terminal, the first polypeptide may sequentially comprise the first intein fragment, the first fragment of the toxic active region of the toxin and the translocation region of the toxin, wherein the first intein fragment, the first fragment of the toxic active region of the toxin and the translocation region of the toxin may be directly or indirectly linked; from the N-terminal to the C-terminal, the second polypeptide may sequentially comprise the second targeting portion, the second fragment of the toxic active region of the toxin and the second intein fragment, wherein the second targeting portion, the second intein fragment and the second fragment of the toxic active region of the toxin are directly or indirectly linked. Under certain conditions, e.g., when a reducing agent is added into the composition, or when the composition is located in a tumor microenvironment, the first intein fragment interacts with the second intein fragment, so that the second targeting portion and the second toxin fragment (including the second fragment of the toxic active region of the toxin) of the second polypeptide and the first toxin fragment (including the first fragment of the toxic active region of the toxin and the translocation region of the toxin) of the first polypeptide are linked to form immunotoxin. From the N-terminal to the C-terminal, the immunotoxin sequentially comprises the second targeting portion, the second fragment of the toxic active region of the toxin, the first fragment of the toxic active region of the toxin and the translocation region of the toxin, wherein the second targeting portion, the second fragment of the toxic active region of the toxin, the first fragment of the toxic active region of the toxin and the translocation region of the toxin are directly or indirectly linked.

Figure 2:
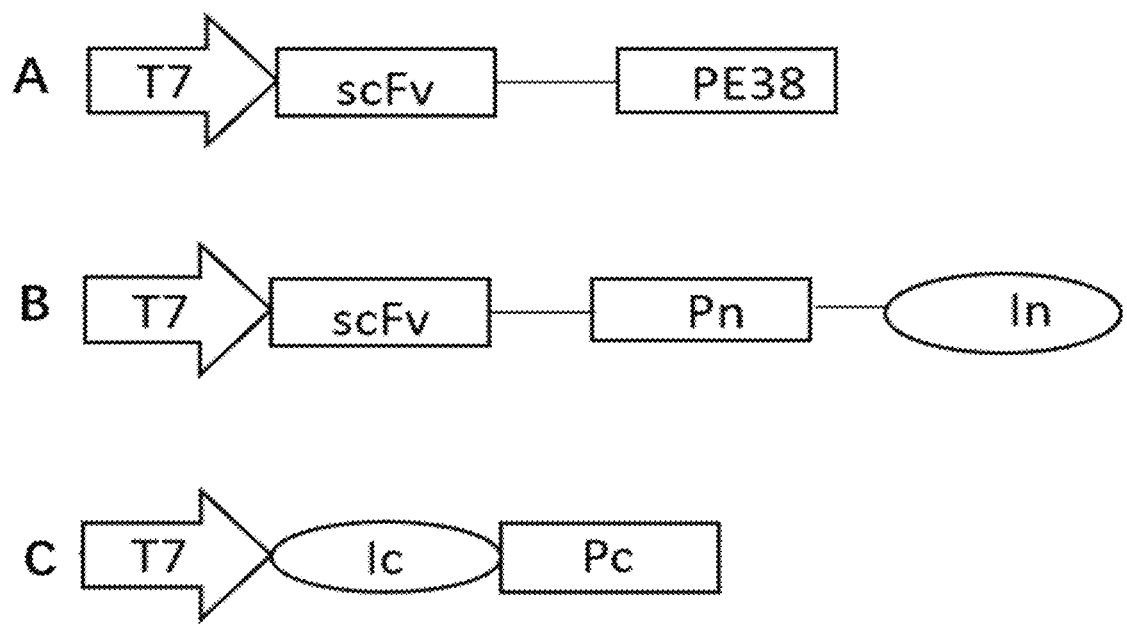
FIG. 2 shows the components of the expression vectors of scFvPM1, scFvPnIn and IcPc of the present application.

For example, in the present application, as shown in FIG. 2, the composition may comprise a first polypeptide and a second polypeptide, the first polypeptide of the present application may comprise a first targeting portion, the second polypeptide may not comprise a targeting portion, the first targeting portion may be ScFv targeting HER2, the toxin utilizes the truncated form PE38. In the first polypeptide (as shown in FIG. 2B), from the N-terminal to the C-terminal, it may sequentially comprise antigen-binding fragment ScFv targeting HER2, the first toxin fragment (Pn) and the first intein fragment (In), wherein the first polypeptide is named ScFvPnIn. In the second polypeptide (as shown in FIG. 2C), from the N-terminal to the C-terminal, it sequentially comprises the second intein fragment (Ic) and the second toxin fragment (Pc), wherein the second polypeptide is named IcPc. Of those, T7 is the promoter of $E.$ $coli$ expression vector. The amino acid residue at the C-terminal of the first toxin fragment is derived from the random coil region of the truncated form PE38, the amino acid residue at the N-terminal of the second toxin fragment is derived from the random coil region of the truncated form PE38. To improve the efficiency of trans-splicing reaction of the split intein, the amino acids at the N-terminal of Pc are subject to site-specific mutagenesis, so that the amino acid residues at sites 1-3 of the N-terminal of Pc are sequentially CFN. By use of scFv targeting HER2, ScFvPnIn can target to the surface of tumor cells. Using the reducibility of tumor microenvironment, the In in ScFvPnIn and the Ic in IcPc undergo trans-splicing reaction of the intein, so that Pn is re-linked to Pc to obtain the immunotoxin ScFvPM1 (as shown in FIG. 2A), which has killing effect on tumor cells. The amino acid sequence of the immunotoxin ScFvPM1 is shown in SEQ ID NO: 10.

In another aspect, the present application provides a method of preparing the composition, including the following steps: 1) providing the first polypeptide; 2) providing the second polypeptide; 3) mixing the first polypeptide with the second polypeptide to give the composition. In the present application, the aforesaid Steps 1, 2 and 3 may or may not take place simultaneously. In the case that Steps 1, 2 and 3 do not take place simultaneously, Step 1 may take place prior to Step 2, or Step 2 may take place prior to Step 1, or Steps 1 and 2 take place simultaneously. In the present application, the molar ratio of the first polypeptide to the second polypeptide in the composition may be 10:1-1:10 (e.g., 10:1-1:10; 9:1-1:9; 8:1-1:8; 7:1-1:7; 6:1-1:6; 5:1-1:5; 4:1-1:4; 3:1-1:3; 2:1-1:2). The composition prepared in accordance with the aforesaid preparation method may comprise the first polypeptide and the second polypeptide, and the first polypeptide and the second polypeptide may be non-biotoxic.

In another aspect, the present application provides a method of preparing the toxin, including the following steps: 1) providing the first polypeptide; 2) providing the second polypeptide; 3) mixing the first polypeptide with the second polypeptide to give the toxin.

In the present application, the non-biotoxic first polypeptide and the non-biotoxic second polypeptide may be mixed to give a toxin with biotoxicity. In the preparation method of the present application, the mixing in Step 3) further comprises adding a reducing agent for mixing. In the present application, after the reducing agent is added, trans-splicing may take place between the first intein fragment in the first polypeptide and the second intein fragment in the second polypeptide, so that the first toxin fragment of the first polypeptide and the second toxin fragment of the second polypeptide may form a toxin with biotoxicity.

In the present application, the preparation method may further comprise adding a reducing agent. In the present application, the step of adding a reducing agent may or may not take place simultaneously with be the aforesaid Steps 1, 2 and 3. In the present application, the term "reducing agent" generally refers to a substance that loses or deviates from electrons in a redox reaction. In the present application, after the reducing agent is added, the first intein fragment in the first polypeptide and the second intein fragment in the second polypeptide may undergo trans-splicing, so that the first toxin fragment in the first polypeptide and the second toxin fragment in the second polypeptide form a toxin with biological toxicity. In the present application, the composition may comprise a toxin with biological toxicity and/or an immunotoxin with biological toxicity after the reducing agent is added.

In the present application, the reducing agent may be selected from the group consisting of: DTT and β-mercaptoethanol. For example, the reducing agent may be DTT and β-mercaptoethanol. For example, the reducing agent may be DTT. For example, the reducing agent may be β-mercaptoethanol.

In the present application, the concentration of the reducing agent in the composition may be 0.001-10000 nM, e.g., 0.001-10000 nM; 0.002-5000 nM; 0.003-2000 nM; 0.005-1000 nM; 0.01-500 nM; 0.015-200 nM; 0.02-100 nM; 0.05-80 nM; 0.1-50 nM; 0.5-20 nM; or 0.1-10 nM. The reducing agent may be added simultaneously with or after the mixing in Step 3.

In the present application, the preparation method may further comprise incubating the composition after adding the reducing agent. In the present application, the term "incubate" generally refers to allow the mixed samples to stand at a certain temperature. In the present application, after adding the reducing agent, the mixture including the first polypeptide, the second polypeptide and the reducing agent may stand at a certain temperature for a certain period.

In the present application, the incubation temperature may be 1° C.-50° C., e.g., 1° C.-50° C., 4° C.-50° C., 4° C.-45° C., 4° C.-40° C., 4° C.-37° C., 8° C.-37° C., 13° C.-37° C., 17° C.-37° C., 17° C.-35° C., 17° C.-30° C., 17° C.-25° C., 17° C.-23° C. or 20° C.-23° C. In the present application, the incubation time may be 2-120 minutes, e.g., 2-120 minutes, 2-100 minutes, 2-80 minutes, 3-80 minutes, 4-80 minutes, 5-80 minutes, 10-80 minutes, 15-80 minutes, 20-80 minutes, 20-80 minutes, 40-80 minutes, 50-80 minutes, 50-70 minutes or 50-60 minutes. For example, at a temperature of 1° C.-50° C., the mixture including the first polypeptide, the second polypeptide and the reducing agent may stand for 2-120 minutes, 2-100 minutes, 2-80 minutes, 4-80 minutes, 5-80 minutes, 10-80 minutes, 15-80 minutes, 20-80 minutes, 20-80 minutes, 40-80 minutes, 50-80 minutes or 50-70 minutes. For example, at a temperature of 4° C.-45° C., the mixture including the first polypeptide, the second polypeptide and the reducing agent may stand for 2-120 minutes, 2-100 minutes, 2-80 minutes, 4-80 minutes, 5-80 minutes, 10-80 minutes, 15-80 minutes, 20-80 minutes, 20-80 minutes, 40-80 minutes, 50-80 minutes or 50-70 minutes. For example, at a temperature of 4° C.-37° C., the mixture including the first polypeptide, the second polypeptide and the reducing agent may stand for 2-120 minutes, 2-100 minutes, 2-80 minutes, 4-80 minutes, 5-80 minutes, 10-80 minutes, 15-80 minutes, 20-80 minutes, 20-80 minutes, 40-80 minutes, 50-80 minutes or 50-70 minutes. For example, at a temperature of 17° C.-37° C., the mixture including the first polypeptide, the second polypeptide and the reducing agent may stand for 2-120 minutes, 2-100 minutes, 2-80 minutes, 4-80 minutes, 5-80 minutes, 10-80 minutes, 15-80 minutes, 20-80 minutes, 20-80 minutes, 40-80 minutes, 50-80 minutes or 50-70 minutes. For example, at a temperature of 4° C.-17° C., the mixture including the first polypeptide, the second polypeptide and the reducing agent may stand for 2-120 minutes, 2-100 minutes, 2-80 minutes, 4-80 minutes, 5-80 minutes, 10-80 minutes, 15-80 minutes, 20-80 minutes, 20-80 minutes, 40-80 minutes, 50-80 minutes or 50-70 minutes.

The composition of the present application may have one or more of the following characteristics: 1) the composition may be divided into the non-toxic first polypeptide and the second polypeptide, which may be administered separately and restore the toxicity at the desired target (such as the tumor microenvironment), which may improve the drug safety and reduce the non-specific toxicity of the composition to normal cells; 2) the composition may be relatively flexibly and adjustably divided into the first polypeptide and the second polypeptide, which may be, e.g., administered by different administration methods, doses and different administration combination methods, so as to achieve a better therapeutic effect; 3) the first polypeptide and the second polypeptide of the composition may be linked via an intein to prepare an active (such as toxic) substance by a preparation method having universal applicability and capable of being applied to various types of compositions, e.g., immunotoxins or protein drugs; 4) when the composition is divided into two portions, that is, the first polypeptide and the second polypeptide with no toxicity, the cleaved two portions may be respectively expressed by prokaryotic or eukaryotic cells, and the two expressed portions have no toxic effect on the host cells, for example, when the immunotoxins are in the combination mode of intact antibody linked to toxin, expression by eukaryotic cells facilitates the assembling of the antibody; and 5) with respect to different tumor associated antigens, the composition may comprise different antibody targeting portions, which may improve the targeting specificity of the composition.

Vector, Cell, Kit and Use

In another aspect, the present application provides a vector, which may comprise a nucleic acid encoding the first polypeptide, and/or, may comprise a nucleic acid encoding the second polypeptide. For example, the vector may comprise a nucleic acid encoding the first polypeptide and a nucleic acid encoding the second polypeptide. For example, the vector may comprise a nucleic acid encoding the first polypeptide. For example, the vector may comprise a nucleic acid encoding the second polypeptide.

The vector may further comprise other genes, e.g., a marker gene that allows selecting the vector in a suitable host cell and under suitable conditions. Moreover, the vector may further comprise an expression control element that allows the coding region to be properly expressed in a suitable host. Such control element is well-established for persons skilled in the art, e.g., may include promoters, ribosome binding sites, enhancers and other control elements that regulate gene transcription or mRNA translation. In some embodiments, the expression control sequence is an adjustable element. The specific structure of the expression control sequence may vary depending on the function of the species or cell types, but usually comprises 5' untranscribed sequence and 5' and 3' untranslated sequences involved in the initiation of transcription and translation, respectively, e.g., TATA box, capped sequence, CAAT sequence, etc. For example, 5' untranscribed expression control sequence may comprise a promoter region, and the promoter ma include a promoter sequence for transcriptionally controlling the functionally linking nucleic acids. The expression control sequence may also comprise an enhancer sequence or an upstream activator sequence. In the present application, suitable promoters may comprise, for example, a promoter for SP6, T3 and T7 polymerases, a human U6RNA promoter, a CMV promoter and an artificial heterozygous promoter thereof (such as CMV), wherein a portion of the promoter may be fused with a portion of the promoter of other cell protein genes (such as human GAPDH, glyceraldehyde-3-phosphate dehydrogenase), which may or cannot comprise additional introns.

The vector may comprise, e.g., plasmid, cosmid, virus, phage or other vectors which are commonly used in, e.g., genetic engineering. For example, the vector is an expression vector. In another aspect, the present application provides a cell, which may express the first polypeptide, and/or may express the second polypeptide. For example, the present application provides a cell, which may express the first polypeptide and the second polypeptide. For example, the present application provides a cell that may express the first polypeptide. For example, the present application provides a cell that may express the second polypeptide. In some embodiments, each type of cell or each cell may comprise one or one type of the nucleic acid molecule or the vector of the present application. In some embodiments, each type or cell or each cell may comprise a plurality of (e.g., 2 or greater) or many type (e.g., 2 or greater) of the nucleic acid molecules or the vectors of the present application. For example, the vector of the present application may be introduced into the cell, e.g., *E. coli* cell or the like. The vector of the present application may be introduced into the cells by well-known methods in the art, e.g., electroporation, lipofectine transfection, lipofectamin transfection, or the like.

In another aspect, the present application provides a kit, which may include a first polypeptide and a second polypeptide. In the present application, the first polypeptide and the second polypeptide may not be mixed with each other in the kit, that is, the first polypeptide and the second polypeptide are separately placed in the kit and are not mixed with each other. In the present application, the first polypeptide and the second polypeptide may be located in different containers, e.g., the first polypeptide is placed in a container, while the second polypeptide is placed in another container, wherein the aforesaid two containers are separate from each other, so that the second polypeptide and the second polypeptide are not mixed with each other.

In the present application, the kit may further comprise a reducing agent. In the present application, the kit may comprise a first polypeptide, a second polypeptide and a reducing agent. In the present application, the reducing agent may be selected from the group consisting of DTT and β-mercaptoethanol. For example, the kit may comprise a first polypeptide, a second polypeptide and DTT. For example, the kit may comprise a first polypeptide, a second polypeptide and β-mercaptoethanol. For example, the kit may comprise a first polypeptide, a second polypeptide, β-mercaptoethanol and DTT.

In the present application, the reducing agent may be contained in a separate container. For example, the container for holding the reducing agent and the container(s) for holding other ingredients (such as, the first polypeptide and the second polypeptide) are separate from each other, that is to say, the container(s) for holding the first polypeptide and the second polypeptide cannot be used to hold the reducing agent, and the reducing agent and other ingredients (such as, the first polypeptide and the second polypeptide) are placed separately.

In the present application, the kit may comprise a composition including a first polypeptide and a second polypeptide, wherein the first polypeptide may comprise a first toxin fragment and a first intein fragment, the second polypeptide may comprise a second toxin fragment and a second intein fragment. Before the first intein fragment interacts with the second intein fragment, both the first polypeptide and the second polypeptide in the composition are non-biotoxic.

The ingredients of the kit of the present application may be contained in separate containers (i.e., a kit having separate parts), or provided in a single container. Moreover, the kit of the present application may further comprise the composition and/or an instruction for performing the method. The instructions may be provided as a user handbook in paper or electronic form. For example, the handbook may comprise instructions for explaining the results obtained from performing the aforesaid method by using the kit of the present application or using the composition.

In another aspect, the present application provides use of the composition, the kit, the vector and/or the cell in preparation of a medicament for treating disease, wherein the disease may comprise tumor. In the present application, the tumors may be selected from the group consisting of: breast cancer, melanoma, ovarian cancer, colon cancer, mesothelioma, glandular tumor, pancreatic cancer and bladder cancer. In the present application, the medicament may be used to treat disease including tumor, e.g., to treat breast cancer, melanoma, ovarian cancer, colon cancer, mesothelioma, glandular tumor, pancreatic cancer and/or bladder cancer. For example, the pharmaceutical composition of the present application may inhibit or delay the development or progression of the disease including the tumor, may reduce the tumor size (or even substantially eliminate the tumor), and/or may alleviate and/or stabilize the conditions.

In another aspect, the present application provides the composition, the kit, the vector and/or the cell, for use intreating tumor. In the present application, treating tumor refers to inhibiting the tumor growth, reducing the tumor size (or even substantially eliminating the tumor), and/or alleviating and/or stabilizing the conditions.

In another aspect, the present application provides a method of treating tumor, including administering the composition, the kit, the vector and/or the cell. In the present application, the administration modes comprise oral administration, intravenous administration, intramuscular administration, in-situ intratumoral administration, inhalation, rectal administration, vaginal administration, transdermal administration, and/or administration via subcutaneous repository. The present application further provides a method of administering the composition, which may include the following steps: mixing the first polypeptide with the second polypeptide and the reducing agent for administration. Under in vitro conditions, the first polypeptide and the second polypeptide may form a toxin or immunotoxin with biotoxicity under reducing conditions, which may, e.g., produce killing or apoptosis effect on the cells.

The present application further provides a method of treating tumor including administering a subject the first polypeptide and the second polypeptide. Under in vivo conditions, the first polypeptide and the second polypeptide may form a toxin with biotoxicity or immunotoxin under tumor cell microenvironment conditions, which may, e.g., produce killing or apoptosis effect on the tumor cells.

In the present application, different portions of the composition may be administered at different time. For example, different portions may be administered at intervals of 1 second, 1 minute, 1 hour, 10 hours, 1 day or longer. In some cases, different portions of the composition may be administered simultaneously. Different portion of the composition of the present application may be administered in the same or different modes, or may be administered in the same or different doses. Different portions of the composition of the present application may be flexibly and adjustably administered, as long as the desired therapeutic effect may be achieved.

EXAMPLES

Example 1. Construction of Expression Vector

To screen a suitable cleavage site of the toxin, it is first required to subject the immunotoxin scFvPE38 to site-specific mutagenesis, wherein the amino acid sequence of the immunotoxin scFvPE38 is as shown in SEQ ID NO:9. The three amino acids downstream of the selected site were mutated in a manner of site-specific mutagenesis. The mutated immunotoxin and its vector are named scFvPM1, scFvPM2 and scFvPM3, respectively. The vectors scFvPM1, scFvPM2 and scFvPM3 were used to express the mutated immunotoxins and purify the target proteins. The obtained mutants scFvPM1, scFvPM2 and scFvPM3 have amino acid sequences as set forth in SEQ ID NO: 10 (wherein the amino acid sequence of the truncated PM1 is shown in SEQ ID NO: 16), SEQ ID NO: 11 and SEQ ID NO: 12, respectively.

Figure 3:
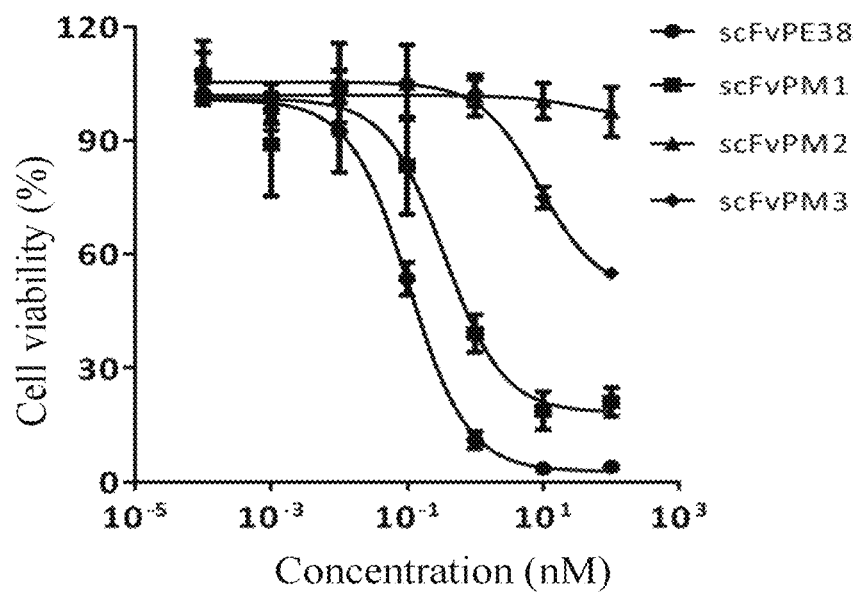
FIG. 3 shows the effect of the mutant of the immunotoxin of the present application on the SKOV3 cell viability.

HER2 antigen-positive SKOV3 cells were treated with the mutants scFvPM1, scFvPM2 and scFvPM3 to investigate the effect of different mutants on cell viability. As shown in FIG. 3, the mutant scFvPM1 has higher cytotoxicity than other mutants. Therefore, the mutation site corresponding to scFvPM1 was selected as the cleavage site of the toxin, the mutation site is also the insertion site of the split intein, and the mutant sequence corresponding to the three amino acids downstream of the selected site was the "CFN" sequence.

At the selected site, scFvPM1 was cleaved into two parts of sequences: scFvPn and Pc. The amino acid sequence of scFvPn was set forth in SEQ ID NO: 13, and the amino acid sequence of Pc was set forth in SEQ ID NO: 14. The scFvPn was fused with the N-terminal of the split intein Npu DnaE (briefly, In), and the C-terminal of Npu DnaE (briefly, Ic) was fused with Pc. The amino acid sequence of In was set forth in SEQ ID NO: 2, and the amino acid sequence of Ic was set forth in SEQ ID NO: 3. The target fragment was synthesized by PCR (polymerase chain reaction), while initiation codon, stop codon and restriction enzyme sites (such as, NdeI/HindIII or the like) were introduced at both ends of the target fragment, respectively. The target fragments were ligated to E. coli expression vector pET28a containing T7 promoter by enzyme digestion and ligation to give the target vector pET-scFvPnIn (as shown in FIG. 2B) and pET-IcPc (as shown in FIG. 2C).

Example 2. Expression and Purification of Protein

PET-scFvPnIn and pET-IcPc vector plasmids were transformed into competent BL21 (DE3) of E. coli, respectively. The monoclonal population was picked and shaken. 100 μg/ml of ampicillin was added to the LB medium, and the cells were cultured at 37° C. to the logarithmic phase (OD600=0.6). An inducing agent, IPTG (isopropyl thiogalactoside), was added to a final concentration of 1 mmol/l to induce the protein expression. After induction at 37° C. for 4 h, the bacteria were collected by centrifugation at 5000 rpm for 5-10 min, washed with 1×PBS buffer, and collected by centrifugation at 5000 rpm for 5-10 min. The bacteria were lysed by a high-pressure homogenizer, and centrifuged for collecting the inclusion body precipitation. The inclusion body precipitation was washed twice with PBS buffer containing 1M guanidine hydrochloride, and then dissolved in PBS buffer containing 6M guanidine hydrochloride. The dissolved inclusion body was added into 50× volume of reconstruction solution (100 mM Tris HCl, 500 mm arginine, 1 mM EDTA disodium, 1 mM reduced glutathione, 0.1 mM oxidized glutathione, pH 9.0-9.5).

After reconstruction by dilution, the protein solution was subject to affinity purification by capto L and His-trap columns. scFvPnIn was purified by capto L column, eluted with citric acid buffer, and then neutralized immediately with 1M Tris HCl buffer at pH9.0. IcPc was purified by His-trap column, and eluted with different concentrations of imidazole buffer. The elution components were collected and analyzed by SDS-PAGE for protein purity. The protein was concentrated by centrifugation with MILLIPORE Amicon Ultra (10MWCO) ultrafiltration tube, and replaced with PBS buffer. The protein was cryopreserved at −20° C. or −80° C. The amino acid sequence of the scFvPnIn obtained from expression is set forth in SEQ ID No: 6, and the amino acid sequence of IcPc is set forth in SEQ ID NO: 15, respectively.

Example 3. In Vitro Trans-Splicing Reaction

Figure 4:
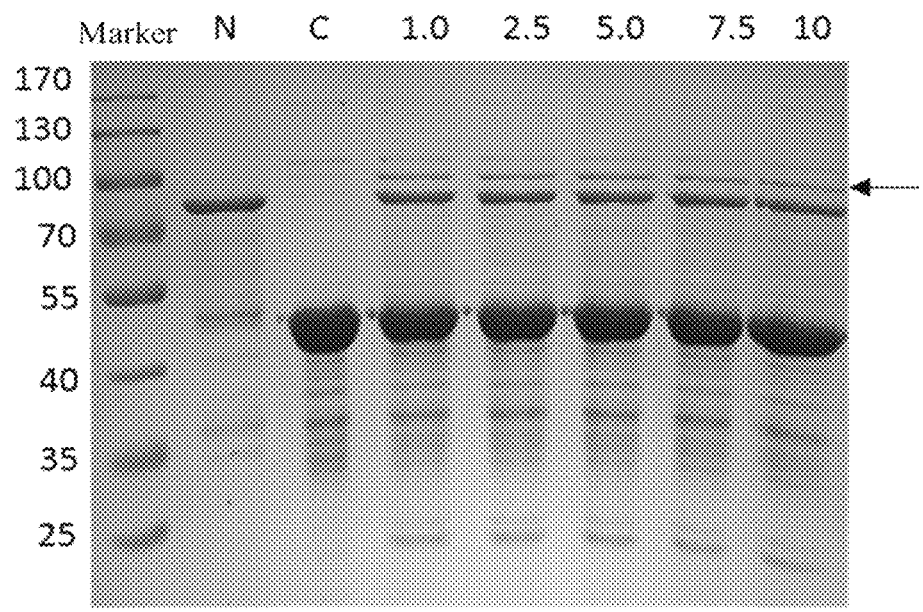
FIG. 4 shows the trans-splicing status mediated by the split intein at different DTT concentrations.

The split intein mediates the protein trans splicing reaction between the two parts of immunotoxin. The two protein parts of scFvPnIn and IcPc purified in Example 2 were mixed at a molar ratio of 1:1, and to the mixture were added 1.0 mM DTT, 2.5 mM DTT, 5.0 mM DTT, 7.5 mM DTT and 10.0 mM DTT, respectively. The mixture was incubated at 37° C. for 30 min. The results are shown in FIG. 4. "N" refers to the sample with scFvPnIn added only, "C" refers to the sample with IcPc added only, "1.0", "2.5", "5.0", "7.5" and "10.0" refer to the samples with 1.0 mM DTT, 2.5 mM DTT, 5.0 mM DTT, 7.5 mM DTT and 10.0 mM DTT added, respectively. The results show that when 1.0 mM DTT was added, scFvPnIn and IcPc rapidly undergo a trans splicing reaction, and obvious bands appear at 85 KD (see the arrow in FIG. 4).

Figure 5:
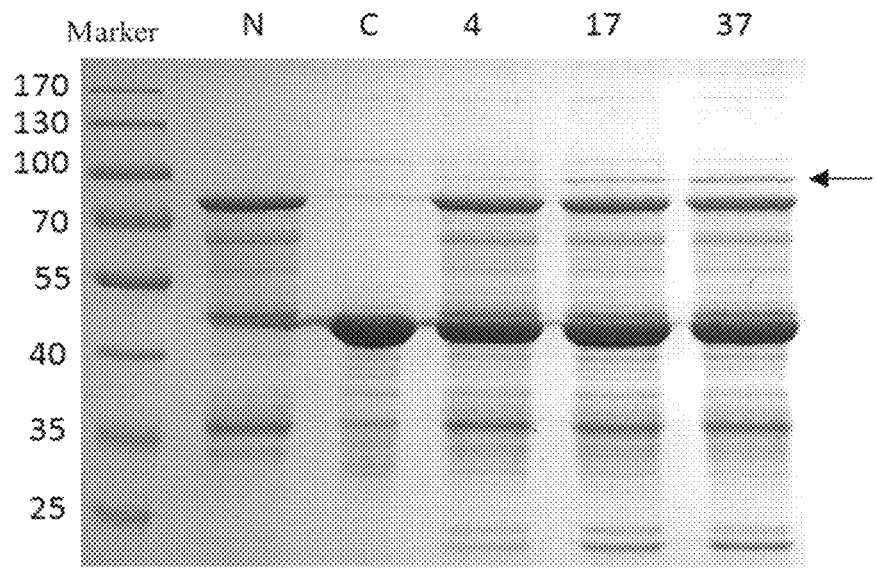
FIG. 5 shows the trans-splicing status mediated by the split intein at different temperatures.

The two parts of scFvPnIn and IcPc purified in Example 2 were mixed at a molar ratio of 1:1, and to the mixture was added 1.0 mM DTT at the same time. Then, the above mixture was incubated at 4° C., 17° C. and 37° C. for 30 min, respectively. The results are shown in FIG. 5. "N" refers to the sample with only scFvPnIn added, and "C" refers to the sample with only IcPc added. Samples "4", "7" and "37" correspond to the samples placed at 4° C., 17° C. and 37° C., respectively. The results showed that the trans-splicing reaction could take place when standing at 4° C., and the reaction efficiency was higher at 17° C. and 37° C., and obvious bands appear at 85 KD (see the arrow in FIG. 5), indicating that an intact immunotoxin was produced.

Figure 6:
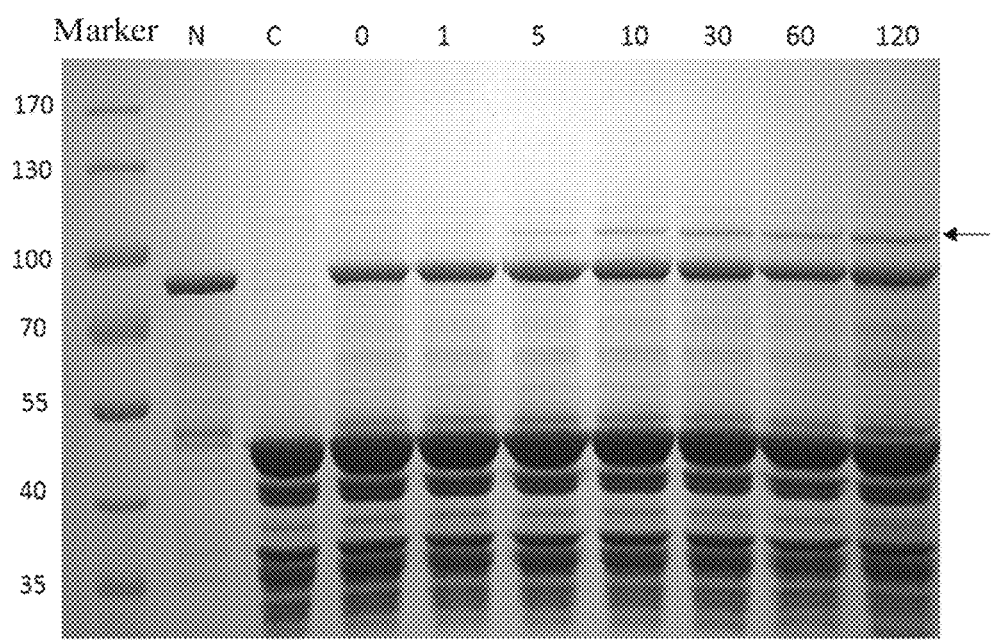
FIG. 6 shows the trans-splicing status mediated by the split intein for different reaction time.

The two parts of scFvPnIn and IcPc purified in Example 2 were mixed at a molar ratio of 1:1, and to the mixture was added 1.0 mM DTT at the same time. Then the above mixture was placed at 37° C. for 0 min, 1 min, 5 min, 10 min, 30 min, 60 min and 120 min, respectively. The results are shown in FIG. 6, and obvious bands appear at 85 KD (see the arrow in FIG. 6). "N" refers to the sample with only scFvPnIn added, "C" refers to the sample with only IcPc added, and "0", "1", "5", "10", "30", "60" and "120" refer to the sample standing for 0 min, 1 min, 5 min, 10 min, 30 min, 60 min and 120 min, respectively. The results showed that the trans splicing reaction could take place at 5 min to produce an intact immunotoxin. The reaction reached the plateau at 60 min. At the end of the reaction, the thiol compounds were required to be removed. The reaction could be quenched by adding a protein loading buffer (60 mM Tris HCl, pH 6.8; 2% SDS; 0.1% bromophenol blue; 25% glycerol, 14.4 mM β-mercaptoethanol). At the end of the reaction, samples were taken for SDS-PAGE detection.

Example 4. Immunotoxin Antigen Affinity Analysis

Figure 7:
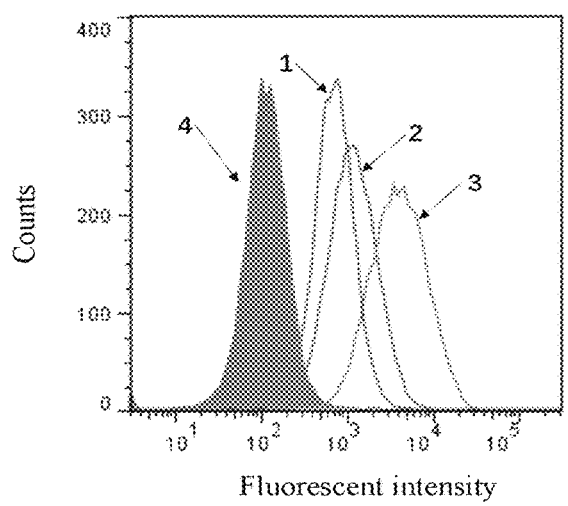
FIG. 7 shows the affinity of the intact immunotoxin and the cleavage immunotoxin to the SKOV3 cell surface antigens.

The antigen affinity of immunotoxin was analyzed by flow cytometry. The subjects were the intact immunotoxin and the N part of the immunotoxin after cleavage. The tumor cells SKOV3 with high antigen expression were treated with the intact immunotoxin and the N part of the cleaved immunotoxin, respectively. After incubation on ice for 1 hour, the cells were washed with PBS, and then the cells were treated by adding anti-toxin antibody (rabbit anti-ETA). After incubation on ice for 1 h, the cells were washed with PBS, and then treated with fluorescently labeled second antibody (Alexa488-anti rabbit IgG). After incubation on ice for 1 h, the cells were washed with PBS and analyzed by flow cytometry. In addition, PBS was set as "control sample" and Herceptin was set as positive control. As shown in FIG. 7, samples "1", "2", "3" and "4" refer to "scFvPnIn", "scFvPM1", "Herceptin" and "control sample", respectively. The test results show that both the intact immunotoxin scFvPM1 and the N-part scFvPnIn of the cleaved immunotoxin have obvious antigen affinity for SKOV3 cells.

Example 5. Immunotoxin Entry Analysis

Figure 8:
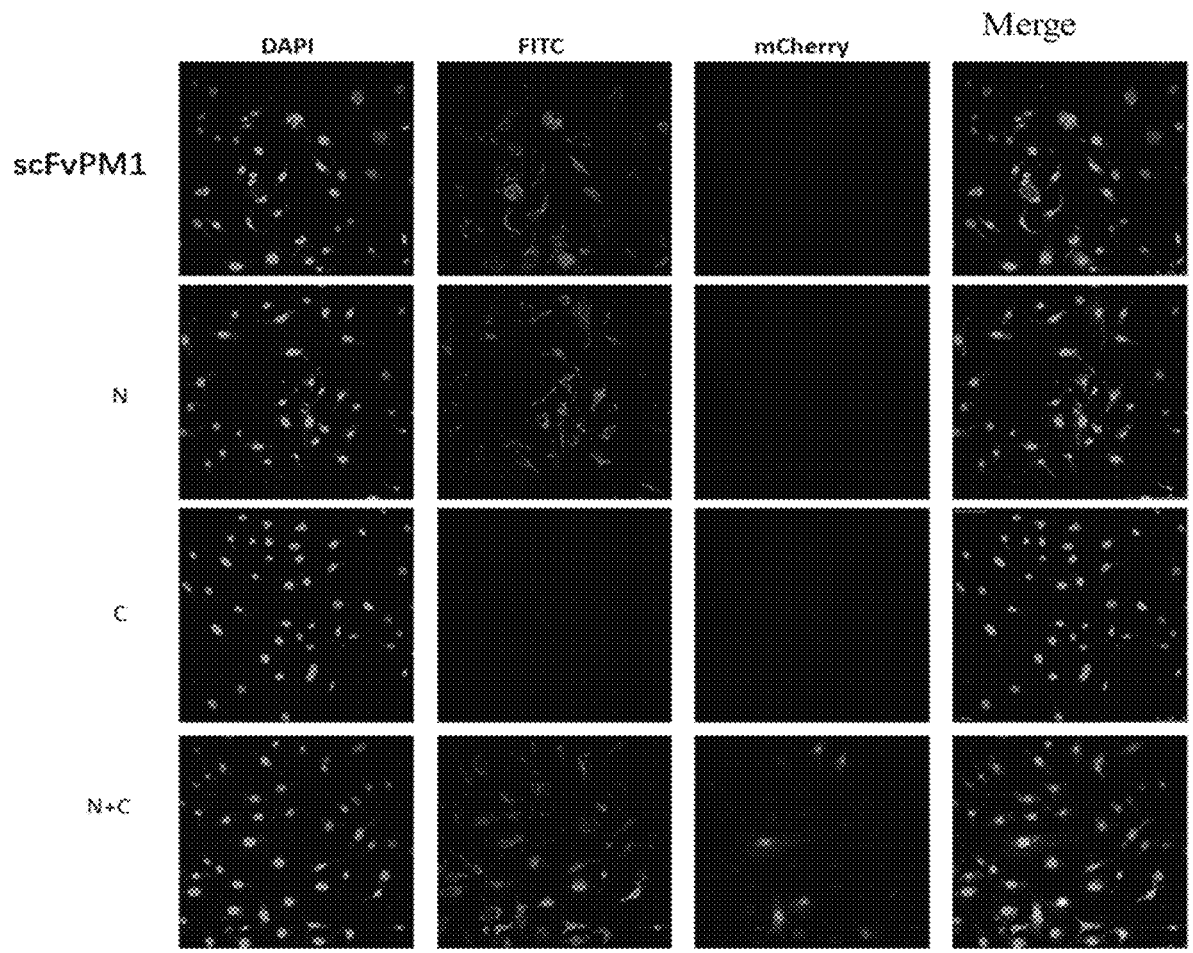
FIG. 8 shows the uptake of SKOV3 cells for the intact immunotoxin and the cleavage immunotoxin.

The uptake of the intact and the cleaved immunotoxins by SKOV3 tumor cells was observed by a confocal laser microscopy. Sterile slides were placed into each well of a 12-well plate. Cells were plated at a density of 5*10⁴/ml, and treated with toxin after culture overnight. Cells were treated by the intact immunotoxin and the cleaved portions of the immunotoxin for 4 h, washed to remove the unbound immunotoxin on the cell surface. The cells were fixed with 4% paraformaldehyde, permeabilized with 0.2% TritonX-100, blocked with 3% BSA, and treated with anti-toxin primary antibody and fluorescently labeled second antibody, respectively. The nuclei were stained with 4,6-bisamidine-2-phenylindole (DAPI). The cell slides were removed and inverted on the slide. The images were observed and photographed under confocal laser microscope. As shown in FIG. 8, "N", "C" and "N+C" refer to individual scFvPnIn, individual IcPc, and mixed scFvPnIn and IcPc (with a reducing agent added), respectively. Both scFvPM1 and scFvPnIn may be labeled with green fluorescent secondary antibody, and IcPc is linked with red fluorescent protein. Therefore, the individual C-part IcPc and the immunotoxin generated by the reaction may show red fluorescence. It can be seen from FIG. 8 that SKOV3 cells uptake more intact immunotoxin, and also obviously uptake the N part, scFvPnIn, in the immunotoxin after cleavage. However, there is no obvious uptake of IcPc in the C part of the immunotoxin after cleavage. When scFvPnIn and IcPc are used in combination, a co-localization area of green and red fluorescence appears in the cells, indicating that the two parts react to generate a new intact immunotoxin.

Example 6. Cytotoxic Analysis of Immunotoxin

Figure 9:
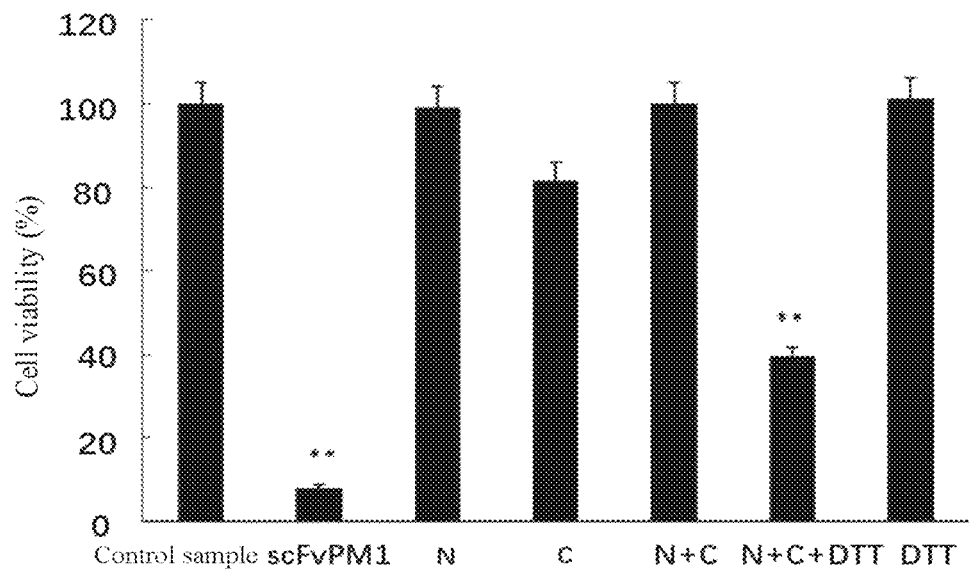
FIG. 9 shows the effect of the intact immunotoxin and the cleavage immunotoxin on the SKOV3 cell viability.
Figure 10:
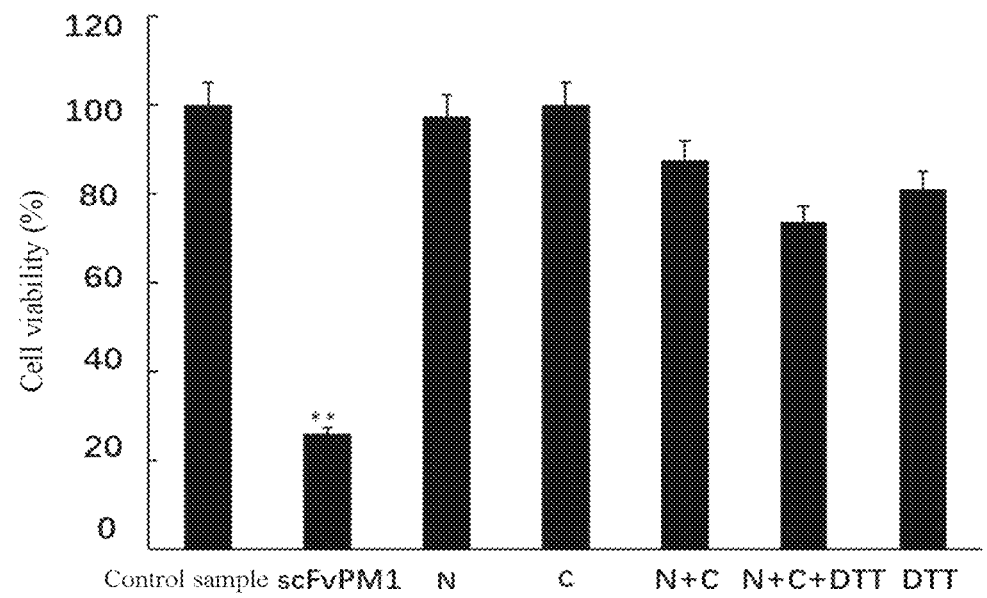
FIG. 10 shows the effect of the intact immunotoxin and the cleavage immunotoxin on the MCF7 cell viability.
Figure 11:
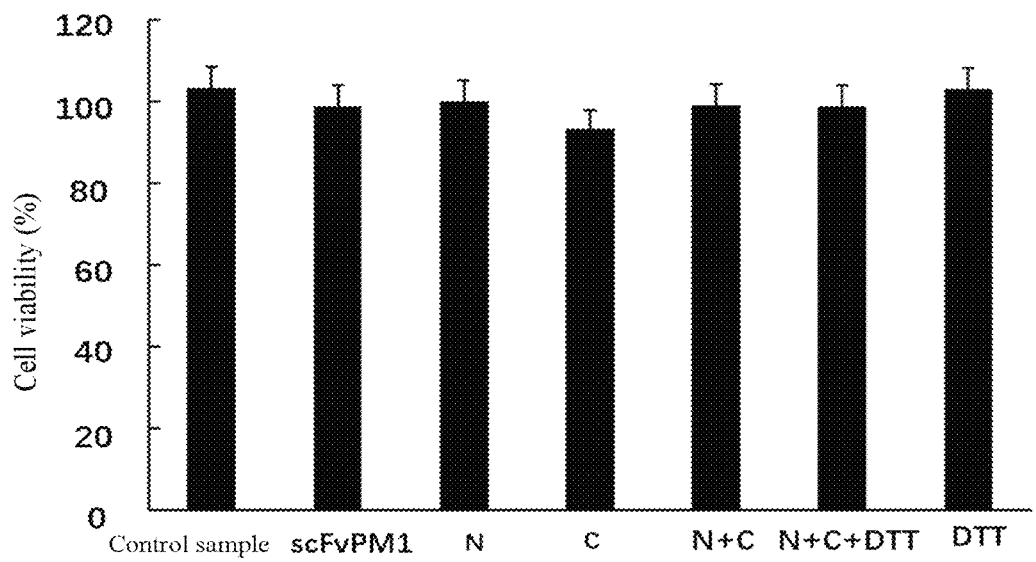
FIG. 11 shows the effect of the intact immunotoxin and the cleavage immunotoxin on the CHO cell viability.
Figure 12:
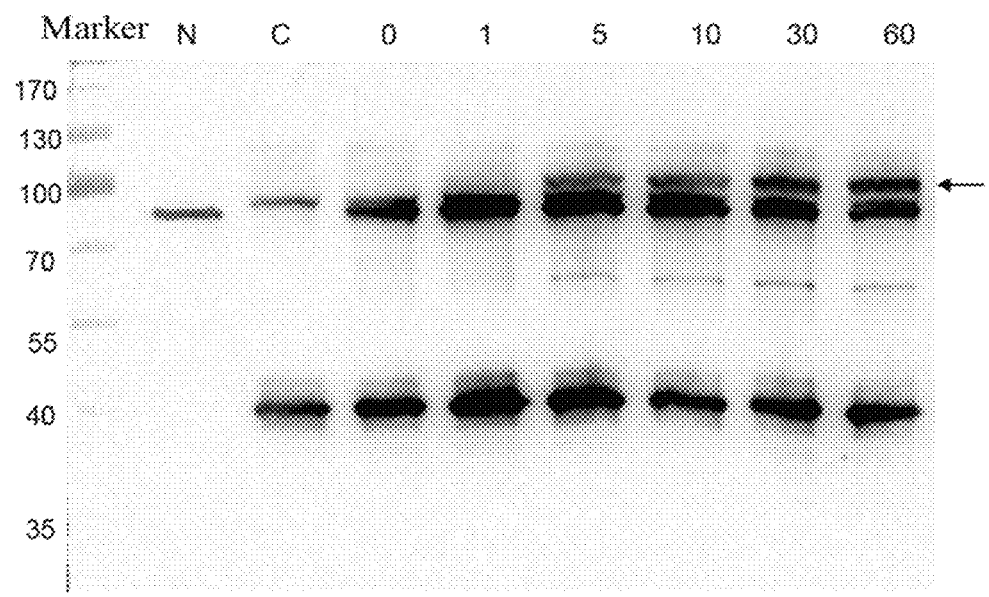
FIG. 12 shows the trans-splicing status of the cleavage immunotoxin mediated by the intein in the cell culturing medium.

SKOV3 cells were treated with non-toxic scFvPnIn and IcPc cleaved from the immunotoxin scFvPM1, alone or in combination, respectively. After 72 hours of treatment, cell viability was detected by CCK8 kit. In FIGS. 9-11, "control sample", "N", "C", "N+C", "N+C+DTT" and "DTT" refer to PBS solution, individual scFvPnIn, individual IcPc, mixed scFvPnIn and IcPc (without reducing agent), mixed scFvPnIn and IcPc (with a reducing agent DTT added) and DTT alone, respectively. As shown in FIG. 9, individual scFvPnIn and IcPc had no effect on cell viability. When scFvPnIn and IcPc were mixed together for use, the cell viability may be reduced under reductive conditions, and an individual reducing agent had no effect on cell viability, indicating that the combination of scFvPnIn and IcPc may generate an intact immunotoxin and restore the cell-killing effect of immunotoxin. The medium of SKOV3 cells was taken for Western blot detection. As shown in FIG. 12, "N" refers to the sample with only scFvPnIn added, "C" refers to the sample with only IcPc added, and "0", "1", "5", "10", "30" and "60" refer to the samples when the medium stand for 0 min, 1 min, 5 min, 10 min, 30 min and 60 min after sample loading, respectively. ScFvPnIn and IcPc were trans spliced to form an intact immunotoxin scFvPM1.

As shown in FIG. 10, the intact immunotoxin also had relatively strong cytotoxicity to MCF7 cells with low HER2 expression, but the cleaved immunotoxin was non-toxic to MCF7 cells. After reassembling of the two-stage toxin, it restored a partial activity, but had relatively low toxicity to MCF7 due to the low expression of antigen.

As shown in FIG. 11, for CHO cells without HER2 antigen expression, neither intact immunotoxin nor cleaved immunotoxin had no cytotoxicity thereto, indicating that the targeting effect of immunotoxin only has selective killing effect on tumor cells expressing HER2 antigen.

Example 7. Immunotoxin Induced Apoptosis

Figure 13:
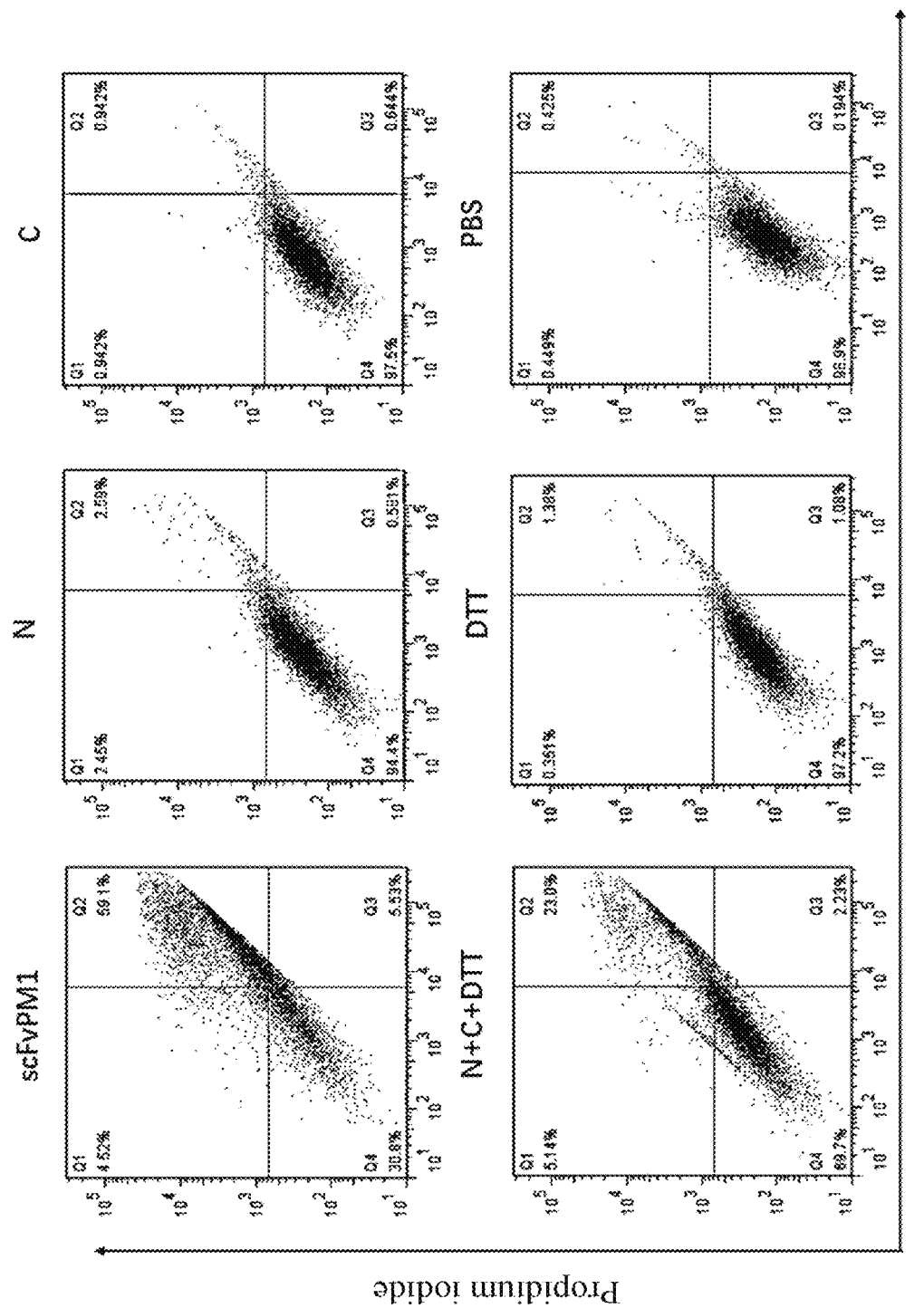
FIG. 13 shows the apoptosis of SKOV3 cells induced by the intact immunotoxin and the cleavage immunotoxin.

The immunotoxin scFvPM1 binds to the cell elongation factor eEF2 after entering the cells. It results in the inactivation due to the occurrence of ADP ribosylation, inhibits the synthesis of cell protein, and causes apoptosis. Now, we investigated the induction of intact immunotoxin and the cleaved portions of immunotoxin in combination on apoptosis. The cells were plated in a 12-well plate with 2×10⁵ cell/well. After cultured overnight, the cells were treated with various immunotoxins for 48 h. The cells were washed to remove culture material on the surface, digested with trypsin to prepare a cell suspension. Then, the cells were treated with AnnexinV-FITC and propidium iodide (PI) for 10 min, respectively. The cells were resuspended in AnnexinV binding buffer and analyzed by a flow cytometry. AnnexinV may selectively bind to phosphatidyl serine on the surface of apoptotic cells. PI cannot pass through the membrane of viable cells, but may pass through the damaged cell membrane and stain the nucleus. Therefore, early apoptotic and late apoptotic cells may be labeled with AnnexinV-FITC and PI, respectively. As shown in FIG. 13, "N", "C", "N+C+DTT", "DTT" and "PBS" refer to individual scFvPnIn, individual IcPc, mixed scFvPnIn and IcPc (adding reducing agent DTT), individual DTT and PBS, respectively. The test results showed that the intact immunotoxin scFvPM1 and the cleaved portions of immunotoxin in combination with DTT added (mixed scFvPnIn and IcPc (with a reducing agent DTT added)) could significantly induce cell apoptosis, while by using the cleaved immunotoxin scFvPnIn or IcPc alone, fewer apoptotic cells could be detected, indicating that the two cleaved portions of immunotoxin were non-toxic.

The foregoing detailed description is provided by way of explanation and illustration, rather than being intended to limit the scope of the appended claims. At present, various changes of the embodiments listed herein are obvious to those skilled in the art, and are reserved within the scope of the appended claims and their equivalents

The invention claimed is:

1. A composition, comprising: a first polypeptide; and a second polypeptide, wherein the first polypeptide comprises a first toxin fragment and a first intein fragment, wherein the second polypeptide comprises a second toxin fragment and a second intein fragment, wherein the first polypeptide is different from the second polypeptide, wherein the first toxin fragment and the second toxin fragment are non-biotoxic, and wherein the first polypeptide and the second polypeptide are capable of making the first toxin fragment and the second toxin fragment to form a toxin with biotoxicity by an interaction between the first intein fragment and the second intein fragment, and wherein the toxin is PE38, which is a truncated form of exotoxin PE from Pseudomonas aeruginosa; wherein the first toxin fragment consists of the amino acid sequence of SEQ ID NO: 4, and the second toxin fragment consists of the amino acid sequence of SEQ ID NO: 14.

2. The composition of claim 1, wherein the first intein fragment is different from the second intein fragment.

3. The composition of claim 1, wherein the first intein fragment and the second intein fragment are derived from a same intein.

4. The composition of claim 3, wherein the intein is a split intein.

5. The composition of any claim 1, wherein in the first polypeptide, the C-terminal of the first toxin fragment is directly or indirectly linked to the N-terminal of the first intein fragment.

6. The composition of claim 5, wherein in the second polypeptide, the N-terminal of the second toxin fragment is directly or indirectly linked to the C-terminal of the second intein fragment.

7. The composition of claim 1, wherein, in the first polypeptide, the N-terminal of the first toxin fragment is directly or indirectly linked to the C-terminal of the first intein fragment.

8. The composition of claim 7, wherein, in the second polypeptide, the C-terminal of the second toxin fragment is directly or indirectly linked to the N-terminal of the second intein fragment.

9. The composition of claim 5, wherein the first intein fragment comprises an N-terminal protein region of a split intein; and wherein the second intein fragment comprises a C-terminal protein region of a split intein.

10. The composition of claim 7, wherein the first intein fragment comprises a C-terminal protein region of a split intein; and wherein the second intein fragment comprises an N-terminal protein region of a split intein.

11. The composition of claim 1, wherein the interaction between the first intein fragment and the second intein fragment comprises a protein trans-splicing of the first intein fragment and the second intein fragment.

12. The composition of claim 1, wherein the first polypeptide and/or the second polypeptide further comprise(s) a targeting portion, and wherein the targeting portion targets a tumor-specific antigen.

13. A method of preparing a composition, comprising:
mixing the first polypeptide with the second polypeptide to obtain the composition of claim 1.

14. The composition according to claim 4, wherein said split intein is selected from the group consisting of SsP DnaB, Ssp DnaE and Npu DnaE.

15. The composition according to claim 5, wherein the first intein fragment comprises the amino acid sequence of SEQ ID NO: 2.

16. The composition according to claim 5, wherein the second intein fragment comprises the amino acid sequence of SEQ ID NO: 3.

17. The composition according to claim 5, wherein the first polypeptide comprises the amino acid sequence of SEQ ID NO: 6.

18. The composition according to claim 5, wherein the second polypeptide comprises the amino acid sequence of any one of SEQ ID NO: 7 and SEQ ID NO: 15.

19. The composition according to claim 12, wherein said tumor-specific antigen is selected from the group consisting of HER2, PD-L1, EGFR, mesothelin and Lewis Y.

* * * * *

SEQUENCE LISTING

```
<160> NUMBER OF SEQ ID NOS: 16

<210> SEQ ID NO 1
<211> LENGTH: 344
<212> TYPE: PRT
<213> ORGANISM: Artificial Sequence
<220> FEATURE:
<223> OTHER INFORMATION: Truncated form PE38

<400> SEQUENCE: 1

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Ser
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Ile Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Gly Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
```

```
                275                 280                 285
Gly Trp Pro Leu Ala Glu Arg Thr Val Val Ile Pro Ser Ala Ile Pro
        290                 295                 300
Thr Asp Pro Arg Asn Val Gly Gly Asp Leu Asp Pro Ser Ser Ile Pro
305                 310                 315                 320
Asp Lys Glu Gln Ala Ile Ser Ala Leu Pro Asp Tyr Ala Ser Gln Pro
                325                 330                 335
Gly Lys Pro Pro Lys Asp Glu Leu
            340
```

<210> SEQ ID NO 2
<211> LENGTH: 102
<212> TYPE: PRT
<213> ORGANISM: Artificial Sequence
<220> FEATURE:
<223> OTHER INFORMATION: First intein fragment

<400> SEQUENCE: 2

```
Cys Leu Ser Tyr Glu Thr Glu Ile Leu Thr Val Glu Tyr Gly Leu Leu
1               5                   10                  15
Pro Ile Gly Lys Ile Val Glu Lys Arg Ile Glu Cys Thr Val Tyr Ser
            20                  25                  30
Val Asp Asn Asn Gly Asn Ile Tyr Thr Gln Pro Val Ala Gln Trp His
        35                  40                  45
Asp Arg Gly Glu Gln Glu Val Phe Glu Tyr Cys Leu Glu Asp Gly Ser
    50                  55                  60
Leu Ile Arg Ala Thr Lys Asp His Lys Phe Met Thr Val Asp Gly Gln
65                  70                  75                  80
Met Leu Pro Ile Asp Glu Ile Phe Glu Arg Glu Leu Asp Leu Met Arg
                85                  90                  95
Val Asp Asn Leu Pro Asn
            100
```

<210> SEQ ID NO 3
<211> LENGTH: 36
<212> TYPE: PRT
<213> ORGANISM: Artificial Sequence
<220> FEATURE:
<223> OTHER INFORMATION: Second intein fragment

<400> SEQUENCE: 3

```
Met Ile Lys Ile Ala Thr Arg Lys Tyr Leu Gly Lys Gln Asn Val Tyr
1               5                   10                  15
Asp Ile Gly Val Glu Arg Asp His Asn Phe Ala Leu Lys Asn Gly Phe
            20                  25                  30
Ile Ala Ser Asn
        35
```

<210> SEQ ID NO 4
<211> LENGTH: 139
<212> TYPE: PRT
<213> ORGANISM: Artificial Sequence
<220> FEATURE:
<223> OTHER INFORMATION: First toxin fragment

<400> SEQUENCE: 4

```
Gly Gly Ser Leu Ala Ala Leu Thr Ala His Gln Ala Cys His Leu Pro
1               5                   10                  15
Leu Glu Thr Ph

```
Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
 50                  55                  60

Ala Ser Pro Gly Ser Gly Asp Leu Gly Glu Ala Ile Arg Glu Gln
 65                  70                  75                  80

Pro Glu Gln Ala Arg Leu Ala Leu Thr Leu Ala Ala Ala Glu Ser Glu
                    85                  90                  95

Arg Phe Val Arg Gln Gly Thr Gly Asn Asp Glu Ala Gly Ala Ala Ser
                   100                 105                 110

Gly Pro Ala Asp Ser Gly Asp Ala Leu Leu Glu Arg Asn Tyr Pro Thr
           115                 120                 125

Gly Ala Glu Phe Leu Gly Asp Gly Gly Asp Ile
           130                 135
```

```
<210> SEQ ID NO 5
<211> LENGTH: 205
<212> TYPE: PRT
<213> ORGANISM: Artificial Sequence
<220> FEATURE:
<223> OTHER INFORMATION: Second toxin fragment

<400> SEQUENCE: 5

Ser Phe Ser Thr Arg Gly Thr Gln Asn Trp Thr Val Glu Arg Leu Leu
 1               5                  10                  15

Gln Ala His Arg Gln Leu Glu Glu Arg Gly Tyr Val Phe Val Gly Tyr
                20                  25                  30

His Gly Thr Phe Leu Glu Ala Ala Gln Ser Ile Val Phe Gly Gly Val
            35                  40                  45

Arg Ala Arg Ser Gln Asp Leu Asp Ala Ile Trp Arg Gly Phe Tyr Ile
 50                  55                  60

Ala Gly Asp Pro Ala Leu Ala Tyr Gly Tyr Ala Gln Asp Gln Glu Pro
 65                  70                  75                  80

Asp Ala Arg Gly Arg Ile Arg Asn Gly Ala Leu Leu Arg Val Tyr Val
                    85                  90                  95

Pro Arg Ser Ser Leu Pro Gly Phe Tyr Arg Thr Gly Leu Thr Leu Ala
                   100                 105                 110

Ala Pro Glu Ala Ala Gly Glu Val Glu Arg Leu Ile Gly His Pro Leu
           115                 120                 125

Pro Leu Arg Leu Asp Ala Ile Thr Gly Pro Glu Glu Glu Gly Gly Arg
           130                 135                 140

Leu Glu Thr Ile Leu Gly Trp Pro Leu Ala Glu Arg Thr Val Val Ile
145                 150                 155                 160

Pro Ser Ala Ile Pro Thr Asp Pro Arg Asn Val Gly Gly Asp Leu Asp
                   165                 170                 175

Pro Ser Ser Ile Pro Asp Lys Glu Gln Ala Ile Ser Ala Leu Pro Asp
               180                 185                 190

Tyr Ala Ser Gln Pro Gly Lys Pro Pro Lys Asp Glu Leu
           195                 200                 205
```

```
<210> SEQ ID NO 6
<211> LENGTH: 484
<212> TYPE: PRT
<213> ORGANISM: Artificial Sequence
<220> FEATURE:
<223> OTHER INFORMATION: First polyp

```
<400> SEQUENCE: 6

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Gly Gly Ser Leu Ala Ala Leu Thr Ala His Gln Ala Cys
            245                 250                 255

His Leu Pro Leu Glu Thr Phe Thr Arg His Arg Gln Pro Arg Gly Trp
                260                 265                 270

Glu Gln Leu Glu Gln Cys Gly Tyr Pro Val Gln Arg Leu Val Ala Leu
            275                 280                 285

Tyr Leu Ala Ala Arg Leu Ser Trp Asn Gln Val Asp Gln Val Ile Arg
    290                 295                 300

Asn Ala Leu Ala Ser Pro Gly Ser Gly Gly Asp Leu Gly Glu Ala Ile
305                 310                 315                 320

Arg Glu Gln Pro Glu Gln Ala Arg Leu Ala Leu Thr Leu Ala Ala Ala
                325                 330                 335

Glu Ser Glu Arg Phe Val Arg Gln Gly Thr Gly Asn Asp Glu Ala Gly
            340                 345                 350

Ala Ala Ser Gly Pro Ala Asp Ser Gly Asp Ala Leu Leu Glu Arg Asn
        355                 360                 365

Tyr Pro Thr Gly Ala Glu Phe Leu Gly Asp Gly Gly Asp Ile Cys Leu
    370                 375                 380

Ser Tyr Glu Thr Glu Ile Leu Thr Val Glu Tyr Gly Leu Leu Pro Ile
385                 390                 395                 400

Gly Lys Ile Val Glu Lys Arg Ile Glu Cys Thr Val Tyr Ser Val Asp
                405                 410                 415
```

```
Asn Asn Gly Asn Ile Tyr Thr Gln Pro Val Ala Gln Trp His Asp Arg
            420                 425                 430

Gly Glu Gln Glu Val Phe Glu Tyr Cys Leu Glu Asp Gly Ser Leu Ile
        435                 440                 445

Arg Ala Thr Lys Asp His Lys Phe Met Thr Val Asp Gly Gln Met Leu
    450                 455                 460

Pro Ile Asp Glu Ile Phe Glu Arg Glu Leu Asp Leu Met Arg Val Asp
465                 470                 475                 480

Asn Leu Pro Asn

<210> SEQ ID NO 7
<211> LENGTH: 484
<212> TYPE: PRT
<213> ORGANISM: Artificial Sequence
<220> FEATURE:
<223> OTHER INFORMATION: Second polypeptide comprising targeting portion

<400> SEQUENCE: 7

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Met Ile Lys Ile Ala Thr Arg Lys Tyr Leu Gly Lys Gln
                245                 250                 255

Asn Val Tyr Asp Ile Gly Val Glu Arg Asp His Asn Phe Ala Leu Lys
            260                 265                 270

Asn Gly Phe Ile Ala Ser Asn Cys Phe Asn Thr Arg Gly Thr Gln Asn
        275                 280                 285
```

Trp Thr Val Glu Arg Leu Leu Gln Ala His Arg Gln Leu Glu Glu Arg
        290                 295                 300

Gly Tyr Val Phe Val Gly Tyr His Gly Thr Phe Leu Glu Ala Ala Gln
305                 310                 315                 320

Ser Ile Val Phe Gly Gly Val Arg Ala Arg Ser Gln Asp Leu Asp Ala
                325                 330                 335

Ile Trp Arg Gly Phe Tyr Ile Ala Gly Asp Pro Ala Leu Ala Tyr Gly
                340                 345                 350

Tyr Ala Gln Asp Gln Glu Pro Asp Ala Arg Gly Arg Ile Arg Asn Gly
                355                 360                 365

Ala Leu Leu Arg Val Tyr Val Pro Arg Ser Ser Leu Pro Gly Phe Tyr
370                 375                 380

Arg Thr Gly Leu Thr Leu Ala Ala Pro Glu Ala Ala Gly Glu Val Glu
385                 390                 395                 400

Arg Leu Ile Gly His Pro Leu Pro Leu Arg Leu Asp Ala Ile Thr Gly
                405                 410                 415

Pro Glu Glu Glu Gly Gly Arg Leu Glu Thr Ile Leu Gly Trp Pro Leu
                420                 425                 430

Ala Glu Arg Thr Val Val Ile Pro Ser Ala Ile Pro Thr Asp Pro Arg
                435                 440                 445

Asn Val Gly Gly Asp Leu Asp Pro Ser Ser Ile Pro Asp Lys Glu Gln
450                 455                 460

Ala Ile Ser Ala Leu Pro Asp Tyr Ala Ser Gln Pro Gly Lys Pro Pro
465                 470                 475                 480

Lys Asp Glu Leu

<210> SEQ ID NO 8
<211> LENGTH: 243
<212> TYPE: PRT
<213> ORGANISM: Artificial Sequence
<220> FEATURE:
<223> OTHER INFORMATION: Targeting portion scFv

<400> SEQUENCE: 8

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
                20                  25                  30

Ala Val Ala Trp Tyr Gln Gln Lys Pro Gly Lys Ala Pro Lys Leu Leu
                35                  40                  45

Ile Tyr Ser Ala Ser Phe Leu Tyr Ser Gly Val Pro Ser Arg Phe Ser
50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
                100                 105                 110

Ser Gly Gly Gly Gly Ser Gly Gly Gly Gly Ser Glu Val Gln Leu Val
                115                 120                 125

Glu Ser Gly Gly Gly Leu Val Gln Pro Gly Gly Ser Leu Arg Leu Ser
                130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro

```
                       165                 170                 175
Thr Asn Gly Tyr Thr Arg Tyr Ala Asp Ser Val Lys Gly Arg Phe Thr
                180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Trp Gly Gly
        210                 215                 220

Asp Gly Phe Tyr Ala Met Asp Tyr Trp Gly Gln Gly Thr Leu Val Thr
225                 230                 235                 240

Val Ser Ser

<210> SEQ ID NO 9
<211> LENGTH: 587
<212> TYPE: PRT
<213> ORGANISM: Artificial Sequence
<220> FEATURE:
<223> OTHER INFORMATION: scFvPE38

<400> SEQUENCE: 9

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Gly Gly Ser Leu Ala Ala Leu Thr Ala His Gln Ala Cys
                245                 250                 255

His Leu Pro Leu Glu Thr Phe Thr Arg His Arg Gln Pro Arg Gly Trp
            260                 265                 270

Glu Gln Leu Glu Gln Cys Gly Tyr Pro Val Gln Arg Leu Val Ala Leu
        275                 280                 285
```

-continued

Tyr Leu Ala Ala Arg Leu Ser Trp Asn Gln Val Asp Gln Val Ile Arg
            290                 295                 300

Asn Ala Leu Ala Ser Pro Gly Ser Gly Gly Asp Leu Gly Glu Ala Ile
305                 310                 315                 320

Arg Glu Gln Pro Glu Gln Ala Arg Leu Ala Leu Thr Leu Ala Ala Ala
                325                 330                 335

Glu Ser Glu Arg Phe Val Arg Gln Gly Thr Gly Asn Asp Glu Ala Gly
            340                 345                 350

Ala Ala Ser Gly Pro Ala Asp Ser Gly Asp Ala Leu Leu Glu Arg Asn
            355                 360                 365

Tyr Pro Thr Gly Ala Glu Phe Leu Gly Asp Gly Asp Ile Ser Phe
370                 375                 380

Ser Thr Arg Gly Thr Gln Asn Trp Thr Val Glu Arg Leu Leu Gln Ala
385                 390                 395                 400

His Arg Gln Leu Glu Glu Arg Gly Tyr Val Phe Val Gly Tyr His Gly
                405                 410                 415

Thr Phe Leu Glu Ala Ala Gln Ser Ile Val Phe Gly Gly Val Arg Ala
            420                 425                 430

Arg Ser Gln Asp Leu Asp Ala Ile Trp Arg Gly Phe Tyr Ile Ala Gly
            435                 440                 445

Asp Pro Ala Leu Ala Tyr Gly Tyr Ala Gln Asp Gln Glu Pro Asp Ala
450                 455                 460

Arg Gly Arg Ile Arg Asn Gly Ala Leu Leu Arg Val Tyr Val Pro Arg
465                 470                 475                 480

Ser Ser Leu Pro Gly Phe Tyr Arg Thr Gly Leu Thr Leu Ala Ala Pro
                485                 490                 495

Glu Ala Ala Gly Glu Val Glu Arg Leu Ile Gly His Pro Leu Pro Leu
            500                 505                 510

Arg Leu Asp Ala Ile Thr Gly Pro Glu Glu Gly Gly Arg Leu Glu
            515                 520                 525

Thr Ile Leu Gly Trp Pro Leu Ala Glu Arg Thr Val Val Ile Pro Ser
530                 535                 540

Ala Ile Pro Thr Asp Pro Arg Asn Val Gly Gly Asp Leu Asp Pro Ser
545                 550                 555                 560

Ser Ile Pro Asp Lys Glu Gln Ala Ile Ser Ala Leu Pro Asp Tyr Ala
                565                 570                 575

Ser Gln Pro Gly Lys Pro Pro Lys Asp Glu Leu
            580                 585

<210> SEQ ID NO 10
<211> LENGTH: 587
<212> TYPE: PRT
<213> ORGANISM: Artificial Sequence
<220> FEATURE:
<223> OTHER INFORMATION: scFvPM1

<400> SEQUENCE: 10

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

-continued

```
Gly Ser Arg Ser Gly Thr Asp Phe Thr Leu Thr Ile Ser Ser Leu Gln
 65                  70                  75                  80

Pro Glu Asp Phe Ala Thr Tyr Tyr Cys Gln Gln His Tyr Thr Thr Pro
                 85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Gly Gly Ser Leu Ala Ala Leu Thr Ala His Gln Ala Cys
                245                 250                 255

His Leu Pro Leu Glu Thr Phe Thr Arg His Arg Gln Pro Arg Gly Trp
            260                 265                 270

Glu Gln Leu Glu Gln Cys Gly Tyr Pro Val Gln Arg Leu Val Ala Leu
        275                 280                 285

Tyr Leu Ala Ala Arg Leu Ser Trp Asn Gln Val Asp Gln Val Ile Arg
    290                 295                 300

Asn Ala Leu Ala Ser Pro Gly Ser Gly Gly Asp Leu Gly Glu Ala Ile
305                 310                 315                 320

Arg Glu Gln Pro Glu Gln Ala Arg Leu Ala Leu Thr Leu Ala Ala Ala
                325                 330                 335

Glu Ser Glu Arg Phe Val Arg Gln Gly Thr Gly Asn Asp Glu Ala Gly
            340                 345                 350

Ala Ala Ser Gly Pro Ala Asp Ser Gly Asp Ala Leu Leu Glu Arg Asn
        355                 360                 365

Tyr Pro Thr Gly Ala Glu Phe Leu Gly Asp Gly Gly Asp Ile Cys Phe
    370                 375                 380

Asn Thr Arg Gly Thr Gln Asn Trp Thr Val Glu Arg Leu Leu Gln Ala
385                 390                 395                 400

His Arg Gln Leu Glu Glu Arg Gly Tyr Val Phe Val Gly Tyr His Gly
                405                 410                 415

Thr Phe Leu Glu Ala Ala Gln Ser Ile Val Phe Gly Gly Val Arg Ala
            420                 425                 430

Arg Ser Gln Asp Leu Asp Ala Ile Trp Arg Gly Phe Tyr Ile Ala Gly
        435                 440                 445

Asp Pro Ala Leu Ala Tyr Gly Tyr Ala Gln Asp Gln Glu Pro Asp Ala
    450                 455                 460

Arg Gly Arg Ile Arg Asn Gly Ala Leu Leu Arg Val Tyr Val Pro Arg
465                 470                 475                 480
```

```
Ser Ser Leu Pro Gly Phe Tyr Arg Thr Gly Leu Thr Leu Ala Ala Pro
                485                 490                 495

Glu Ala Ala Gly Glu Val Glu Arg Leu Ile Gly His Pro Leu Pro Leu
            500                 505                 510

Arg Leu Asp Ala Ile Thr Gly Pro Glu Glu Gly Gly Arg Leu Glu
        515                 520                 525

Thr Ile Leu Gly Trp Pro Leu Ala Glu Arg Thr Val Val Ile Pro Ser
    530                 535                 540

Ala Ile Pro Thr Asp Pro Arg Asn Val Gly Asp Leu Asp Pro Ser
545                 550                 555                 560

Ser Ile Pro Asp Lys Glu Gln Ala Ile Ser Ala Leu Pro Asp Tyr Ala
                565                 570                 575

Ser Gln Pro Gly Lys Pro Pro Lys Asp Glu Leu
                580                 585
```

<210> SEQ ID NO 11
<211> LENGTH: 587
<212> TYPE: PRT
<213> ORGANISM: Artificial Sequence
<220> FEATURE:
<223> OTHER INFORMATION: scFvPM2

<400> SEQUENCE: 11

```
Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ser Arg Trp Gly Gly
    210                 215                 220

Asp Gly Phe Tyr Ala Met Asp Tyr Trp Gly Gln Gly Thr Leu Val Thr
225                 230                 235                 240

Val Ser Ser Gly Gly Ser Leu Ala Ala Leu Thr Ala His Gln Ala Cys
                245                 250                 255
```

His Leu Pro Leu Glu Thr Phe Thr Arg His Arg Gln Pro Arg Gly Trp
            260                 265                 270

Glu Gln Leu Glu Gln Cys Gly Tyr Pro Val Gln Arg Leu Val Ala Leu
        275                 280                 285

Tyr Leu Ala Ala Arg Leu Ser Trp Asn Gln Val Asp Gln Val Ile Arg
    290                 295                 300

Asn Ala Leu Ala Ser Pro Gly Ser Gly Gly Asp Leu Gly Glu Ala Ile
305                 310                 315                 320

Arg Glu Gln Pro Glu Gln Ala Arg Leu Ala Leu Thr Leu Ala Ala Ala
                325                 330                 335

Glu Ser Glu Arg Phe Val Arg Gln Gly Thr Gly Asn Asp Glu Ala Gly
            340                 345                 350

Ala Ala Ser Gly Pro Ala Asp Ser Gly Asp Ala Leu Leu Glu Arg Asn
        355                 360                 365

Tyr Pro Thr Gly Ala Glu Phe Leu Gly Asp Gly Asp Ile Ser Phe
    370                 375                 380

Ser Thr Arg Gly Thr Gln Asn Trp Thr Val Glu Arg Leu Leu Gln Ala
385                 390                 395                 400

His Arg Gln Leu Glu Glu Arg Gly Tyr Val Phe Val Gly Tyr His Gly
                405                 410                 415

Thr Phe Leu Glu Ala Ala Gln Ser Ile Val Phe Gly Gly Val Arg Ala
            420                 425                 430

Arg Ser Gln Asp Leu Asp Ala Ile Trp Arg Gly Phe Tyr Ile Ala Gly
        435                 440                 445

Asp Pro Ala Leu Ala Tyr Gly Tyr Ala Gln Asp Gln Glu Pro Cys Phe
    450                 455                 460

Asn Gly Arg Ile Arg Asn Gly Ala Leu Leu Arg Val Tyr Val Pro Arg
465                 470                 475                 480

Ser Ser Leu Pro Gly Phe Tyr Arg Thr Gly Leu Thr Leu Ala Ala Pro
                485                 490                 495

Glu Ala Ala Gly Glu Val Glu Arg Leu Ile Gly His Pro Leu Pro Leu
            500                 505                 510

Arg Leu Asp Ala Ile Thr Gly Pro Glu Glu Glu Gly Gly Arg Leu Glu
        515                 520                 525

Thr Ile Leu Gly Trp Pro Leu Ala Glu Arg Thr Val Val Ile Pro Ser
    530                 535                 540

Ala Ile Pro Thr Asp Pro Arg Asn Val Gly Gly Asp Leu Asp Pro Ser
545                 550                 555                 560

Ser Ile Pro Asp Lys Glu Gln Ala Ile Ser Ala Leu Pro Asp Tyr Ala
                565                 570                 575

Ser Gln Pro Gly Lys Pro Pro Lys Asp Glu Leu
            580                 585

<210> SEQ ID NO 12
<211> LENGTH: 587
<212> TYPE: PRT
<213> ORGANISM: Artificial Sequence
<220> FEATURE:
<223> OTHER INFORMATION: scFvPM3

<400> SEQUENCE: 12

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

```
Ala Val Ala Trp Tyr Gln Gln Lys Pro Gly Lys Ala Pro Lys Leu Leu
         35                  40                  45
Ile Tyr Ser Ala Ser Phe Leu Tyr Ser Gly Val Pro Ser Arg Phe Ser
 50                  55                  60
Gly Ser Arg Ser Gly Thr Asp Phe Thr Leu Thr Ile Ser Ser Leu Gln
 65                  70                  75                  80
Pro Glu Asp Phe Ala Thr Tyr Tyr Cys Gln Gln His Tyr Thr Thr Pro
                 85                  90                  95
Pro Thr Phe Gly Gln Gly Thr Lys Val Glu Ile Lys Gly Gly Gly Gly
            100                 105                 110
Ser Gly Gly Gly Gly Ser Gly Gly Gly Ser Glu Val Gln Leu Val
            115                 120                 125
Glu Ser Gly Gly Gly Leu Val Gln Pro Gly Gly Ser Leu Arg Leu Ser
    130                 135                 140
Cys Ala Ala Ser Gly Phe Asn Ile Lys Asp Thr Tyr Ile His Trp Val
145                 150                 155                 160
Arg Gln Ala Pro Gly Lys Gly Leu Glu Trp Val Ala Arg Ile Tyr Pro
                165                 170                 175
Thr Asn Gly Tyr Thr Arg Tyr Ala Asp Ser Val Lys Gly Arg Phe Thr
            180                 185                 190
Ile Ser Ala Asp Thr Ser Lys Asn Thr Ala Tyr Leu Gln Met Asn Ser
    195                 200                 205
Leu Arg Ala Glu Asp Thr Ala Val Tyr Tyr Cys Ser Arg Trp Gly Gly
    210                 215                 220
Asp Gly Phe Tyr Ala Met Asp Tyr Trp Gly Gln Gly Thr Leu Val Thr
225                 230                 235                 240
Val Ser Ser Gly Gly Ser Leu Ala Ala Leu Thr Ala His Gln Ala Cys
            245                 250                 255
His Leu Pro Leu Glu Thr Phe Thr Arg His Arg Gln Pro Arg Gly Trp
            260                 265                 270
Glu Gln Leu Glu Gln Cys Gly Tyr Pro Val Gln Arg Leu Val Ala Leu
    275                 280                 285
Tyr Leu Ala Ala Arg Leu Ser Trp Asn Gln Val Asp Gln Val Ile Arg
    290                 295                 300
Asn Ala Leu Ala Ser Pro Gly Ser Gly Gly Asp Leu Gly Glu Ala Ile
305                 310                 315                 320
Arg Glu Gln Pro Glu Gln Ala Arg Leu Ala Leu Thr Leu Ala Ala Ala
                325                 330                 335
Glu Ser Glu Arg Phe Val Arg Gln Gly Thr Gly Asn Asp Glu Ala Gly
            340                 345                 350
Ala Ala Ser Gly Pro Ala Asp Ser Gly Asp Ala Leu Leu Glu Arg Asn
            355                 360                 365
Tyr Pro Thr Gly Ala Glu Phe Leu Gly Asp Gly Gly Asp Ile Ser Phe
    370                 375                 380
Ser Thr Arg Gly Thr Gln Asn Trp Thr Val Glu Arg Leu Leu Gln Ala
385                 390                 395                 400
His Arg Gln Leu Glu Glu Arg Gly Tyr Val Phe Val Gly Tyr His Gly
                405                 410                 415
Thr Phe Leu Glu Ala Ala Gln Ser Ile Val Phe Gly Gly Val Arg Ala
            420                 425                 430
Arg Ser Gln Asp Leu Asp Ala Ile Trp Arg Gly Phe Tyr Ile Ala Gly
            435                 440                 445
Asp Pro Ala Leu Ala Tyr Gly Tyr Ala Gln Asp Gln Glu Pro Asp Ala
```

```
            450                 455                 460
Arg Gly Arg Ile Arg Asn Gly Ala Leu Leu Arg Val Tyr Val Pro Arg
465                 470                 475                 480

Ser Ser Leu Pro Gly Phe Tyr Arg Thr Gly Leu Thr Leu Ala Ala Pro
                485                 490                 495

Glu Ala Ala Gly Glu Val Glu Arg Leu Ile Gly His Pro Leu Cys Phe
            500                 505                 510

Asn Leu Asp Ala Ile Thr Gly Pro Glu Glu Gly Gly Arg Leu Glu
            515                 520                 525

Thr Ile Leu Gly Trp Pro Leu Ala Glu Arg Thr Val Val Ile Pro Ser
            530                 535                 540

Ala Ile Pro Thr Asp Pro Arg Asn Val Gly Gly Asp Leu Asp Pro Ser
545                 550                 555                 560

Ser Ile Pro Asp Lys Glu Gln Ala Ile Ser Ala Leu Pro Asp Tyr Ala
                565                 570                 575

Ser Gln Pro Gly Lys Pro Pro Lys Asp Glu Leu
            580                 585

<210> SEQ ID NO 13
<211> LENGTH: 382
<212> TYPE: PRT
<213> ORGANISM: Artificial Sequence
<220> FEATURE:
<223> OTHER INFORMATION: scFvPn

<400> SEQUENCE: 13

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
            130                 135                 140

Cys Ala Ala Ser Gly Phe Asn Ile Lys Asp Thr Tyr Ile His Trp Val
145                 150                 155                 160

Arg Gln Ala Pro Gly Lys Gly Leu Glu Trp Val Ala Arg Ile Tyr Pro
                165                 170                 175

Thr Asn Gly Tyr Thr Arg Tyr Ala Asp Ser Val Lys Gly Arg Phe Thr
            180                 185                 190

Ile Ser Ala Asp Thr Ser Lys Asn Thr Ala Tyr Leu Gln Met Asn Ser
            195                 200                 205

Leu Arg Ala Glu Asp Thr Ala Val Tyr Tyr Cys Ser Arg Trp Gly Gly
        210                 215                 220

Asp Gly Phe Tyr Ala Met Asp Tyr Trp Gly Gln Gly Thr Leu Val Thr
```

```
                    225                 230                 235                 240

Val Ser Ser Gly Gly Ser Leu Ala Ala Leu Thr Ala His Gln Ala Cys
                        245                 250                 255

His Leu Pro Leu Glu Thr Phe Thr Arg His Arg Gln Pro Arg Gly Trp
                    260                 265                 270

Glu Gln Leu Glu Gln Cys Gly Tyr Pro Val Gln Arg Leu Val Ala Leu
                    275                 280                 285

Tyr Leu Ala Ala Arg Leu Ser Trp Asn Gln Val Asp Gln Val Ile Arg
                290                 295                 300

Asn Ala Leu Ala Ser Pro Gly Ser Gly Gly Asp Leu Gly Glu Ala Ile
    305                 310                 315                 320

Arg Glu Gln Pro Glu Gln Ala Arg Leu Ala Leu Thr Leu Ala Ala Ala
                    325                 330                 335

Glu Ser Glu Arg Phe Val Arg Gln Gly Thr Gly Asn Asp Glu Ala Gly
                    340                 345                 350

Ala Ala Ser Gly Pro Ala Asp Ser Gly Asp Ala Leu Leu Glu Arg Asn
                    355                 360                 365

Tyr Pro Thr Gly Ala Glu Phe Leu Gly Asp Gly Asp Ile
                370                 375                 380

<210> SEQ ID NO 14
<211> LENGTH: 205
<212> TYPE: PRT
<213> ORGANISM: Artificial Sequence
<220> FEATURE:
<223> OTHER INFORMATION: Pc

<400> SEQUENCE: 14

Cys Phe Asn Thr Arg Gly Thr Gln Asn Trp Thr Val Glu Arg Leu Leu
    1               5                   10                  15

Gln Ala His Arg Gln Leu Glu Glu Arg Gly Tyr Val Phe Val Gly Tyr
                    20                  25                  30

His Gly Thr Phe Leu Glu Ala Ala Gln Ser Ile Val Phe Gly Gly Val
                35                  40                  45

Arg Ala Arg Ser Gln Asp Leu Asp Ala Ile Trp Arg Gly Phe Tyr Ile
    50                  55                  60

Ala Gly Asp Pro Ala Leu Ala Tyr Gly Tyr Ala Gln Asp Gln Glu Pro
    65                  70                  75                  80

Asp Ala Arg Gly Arg Ile Arg Asn Gly Ala Leu Leu Arg Val Tyr Val
                    85                  90                  95

Pro Arg Ser Ser Leu Pro Gly Phe Tyr Arg Thr Gly Leu Thr Leu Ala
                    100                 105                 110

Ala Pro Glu Ala Ala Gly Glu Val Glu Arg Leu Ile Gly His Pro Leu
                115                 120                 125

Pro Leu Arg Leu Asp Ala Ile Thr Gly Pro Glu Glu Gly Gly Arg
    130                 135                 140

Leu Glu Thr Ile Leu Gly Trp Pro Leu Ala Glu Arg Thr Val Val Ile
    145                 150                 155                 160

Pro Ser Ala Ile Pro Thr Asp Pro Arg Asn Val Gly Gly Asp Leu Asp
                    165                 170                 175

Pro Ser Ser Ile Pro Asp Lys Glu Gln Ala Ile Ser Ala Leu Pro Asp
                    180                 185                 190

Tyr Ala Ser Gln Pro Gly Lys Pro Pro Lys Asp Glu Leu
                195                 200                 205
```

```
<210> SEQ ID NO 15
<211> LENGTH: 241
<212> TYPE: PRT
<213> ORGANISM: Artificial Sequence
<220> FEATURE:
<223> OTHER INFORMATION: Second polypeptide not comprising targeting
      portion (IcPc)

<400> SEQUENCE: 15

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Cys Phe Asn Thr Arg Gly Thr Gln Asn Trp Thr Val
        35                  40                  45

Glu Arg Leu Leu Gln Ala His Arg Gln Leu Glu Glu Arg Gly Tyr Val
    50                  55                  60

Phe Val Gly Tyr His Gly Thr Phe Leu Glu Ala Ala Gln Ser Ile Val
65                  70                  75                  80

Phe Gly Gly Val Arg Ala Arg Ser Gln Asp Leu Asp Ala Ile Trp Arg
                85                  90                  95

Gly Phe Tyr Ile Ala Gly Asp Pro Ala Leu Ala Tyr Gly Tyr Ala Gln
            100                 105                 110

Asp Gln Glu Pro Asp Ala Arg Gly Arg Ile Arg Asn Gly Ala Leu Leu
        115                 120                 125

Arg Val Tyr Val Pro Arg Ser Ser Leu Pro Gly Phe Tyr Arg Thr Gly
    130                 135                 140

Leu Thr Leu Ala Ala Pro Glu Ala Gly Glu Val Glu Arg Leu Ile
145                 150                 155                 160

Gly His Pro Leu Pro Leu Arg Leu Asp Ala Ile Thr Gly Pro Glu Glu
                165                 170                 175

Glu Gly Gly Arg Leu Glu Thr Ile Leu Gly Trp Pro Leu Ala Glu Arg
            180                 185                 190

Thr Val Val Ile Pro Ser Ala Ile Pro Thr Asp Pro Arg Asn Val Gly
        195                 200                 205

Gly Asp Leu Asp Pro Ser Ser Ile Pro Asp Lys Glu Gln Ala Ile Ser
    210                 215                 220

Ala Leu Pro Asp Tyr Ala Ser Gln Pro Gly Lys Pro Pro Lys Asp Glu
225                 230                 235                 240

Leu

<210> SEQ ID NO 16
<211> LENGTH: 344
<212> TYPE: PRT
<213> ORGANISM: Artificial Sequence
<220> FEATURE:
<223> OTHER INFORMATION: Truncated form PM1

<400> SEQUENCE: 16

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60
```

-continued

```
Ala Ser Pro Gly Ser Gly Asp Leu Gly Glu Ala Ile Arg Glu Gln
 65              70                  75                  80

Pro Glu Gln Ala Arg Leu Ala Leu Thr Leu Ala Ala Glu Ser Glu
                 85                  90                  95

Arg Phe Val Arg Gln Gly Thr Gly Asn Asp Glu Ala Gly Ala Ala Ser
                100                 105                 110

Gly Pro Ala Asp Ser Gly Asp Ala Leu Leu Glu Arg Asn Tyr Pro Thr
                115                 120                 125

Gly Ala Glu Phe Leu Gly Asp Gly Gly Asp Ile Cys Phe Asn Thr Arg
                130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
                180                 185                 190

Asp Leu Asp Ala Ile Trp Arg Gly Phe Tyr Ile Ala Gly Asp Pro Ala
                195                 200                 205

Leu Ala Tyr Gly Tyr Ala Gln Asp Gln Glu Pro Asp Ala Arg Gly Arg
210                 215                 220

Ile Arg Asn Gly Ala Leu Leu Arg Val Tyr Val Pro Arg Ser Ser Leu
225                 230                 235                 240

Pro Gly Phe Tyr Arg Thr Gly Leu Thr Leu Ala Ala Pro Glu Ala Ala
                245                 250                 255

Gly Glu Val Glu Arg Leu Ile Gly His Pro Leu Pro Leu Arg Leu Asp
                260                 265                 270

Ala Ile Thr Gly Pro Glu Glu Glu Gly Gly Arg Leu Glu Thr Ile Leu
                275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Lys Asp Glu Leu
                340
```